(12) United States Patent
Kozicki et al.

(10) Patent No.: US 11,598,015 B2
(45) Date of Patent: Mar. 7, 2023

(54) FABRICATION OF DENDRITIC STRUCTURES AND TAGS

(71) Applicant: ARIZONA BOARD OF REGENTS ON BEHALF OF ARIZONA STATE UNIVERSITY, Scottsdale, AZ (US)

(72) Inventors: Michael N. Kozicki, Phoenix, AZ (US); Yago Gonzalez Velo, Tempe, AZ (US); Smitha Swain, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 17/050,750

(22) PCT Filed: Apr. 26, 2019

(86) PCT No.: PCT/US2019/029284
§ 371 (c)(1),
(2) Date: Oct. 26, 2020

(87) PCT Pub. No.: WO2019/210129
PCT Pub. Date: Oct. 31, 2019

(65) Prior Publication Data
US 2021/0230763 A1 Jul. 29, 2021

Related U.S. Application Data

(60) Provisional application No. 62/662,979, filed on Apr. 26, 2018.

(51) Int. Cl.
*C25D 3/38* (2006.01)
*A61K 9/48* (2006.01)
(Continued)

(52) U.S. Cl.
CPC .............. *C25D 3/38* (2013.01); *A61K 9/4891* (2013.01); *C25D 3/46* (2013.01); *C25D 5/48* (2013.01); *C25D 5/605* (2020.08); *C25D 7/00* (2013.01)

(58) Field of Classification Search
CPC ........................................................ C25D 5/48
See application file for complete search history.

(56) References Cited

U.S. PATENT DOCUMENTS 1,256,954 A * 2/1918 Travers .................... C25D 5/44
205/228
1,969,553 A * 8/1934 Gernes ..................... C25D 3/58
205/240

(Continued)

FOREIGN PATENT DOCUMENTS

EP 2237183 10/2010
EP 2973209 1/2016
(Continued)

OTHER PUBLICATIONS

Podsiki, Chart of Heavy Metals, their Salts, and other Compounds (Year: 2008).*
(Continued)

*Primary Examiner* — Ho-Sung Chung
(74) *Attorney, Agent, or Firm* — Fish & Richardson P.C.

(57) ABSTRACT

Methods for fabricating dendritic structures and tags include introducing an electrolyte material onto a substrate, into a substrate, or both onto and into a substrate, and applying an electrical potential to at least one pair of electrodes positioned on the substrate to form one or more dendritic structures on the substrate.

13 Claims, 11 Drawing Sheets

(51) Int. Cl.
  *C25D 3/46* (2006.01)
  *C25D 5/48* (2006.01)
  *C25D 7/00* (2006.01)
  *C25D 5/00* (2006.01)

(56) References Cited

U.S. PATENT DOCUMENTS

| | | |
|---|---|---|
| 4,038,158 A | 7/1977 | Bursey et al. |
| 4,158,807 A | 6/1979 | Senturia |
| 4,586,988 A | 5/1986 | Nath et al. |
| 4,885,227 A | 12/1989 | Nakamura |
| 5,477,088 A | 12/1995 | Rockett et al. |
| 5,761,115 A | 6/1998 | Kozicki et al. |
| 5,896,312 A | 4/1999 | Kozicki et al. |
| 5,914,893 A | 6/1999 | Kozicki et al. |
| 6,036,839 A | 3/2000 | Kohut et al. |
| 6,084,796 A | 7/2000 | Kozicki et al. |
| 6,184,456 B1 | 2/2001 | Matsuyama et al. |
| 6,340,544 B1 | 1/2002 | Akutsu et al. |
| 6,388,324 B2 | 5/2002 | Kozicki |
| 6,418,049 B1 | 7/2002 | Kozicki et al. |
| 6,469,364 B1 | 10/2002 | Kozicki |
| 6,487,106 B1 | 11/2002 | Kozicki |
| 6,635,914 B2 | 10/2003 | Kozicki et al. |
| 6,798,692 B2 | 9/2004 | Kozicki et al. |
| 6,825,489 B2 | 11/2004 | Kozicki |
| 6,865,117 B2 | 3/2005 | Kozicki |
| 6,914,802 B2 | 7/2005 | Kozicki |
| 6,927,411 B2 | 8/2005 | Kozicki |
| 6,940,745 B2 | 9/2005 | Kozicki |
| 6,985,378 B2 | 1/2006 | Kozicki |
| 6,998,312 B2 | 2/2006 | Kozicki et al. |
| 7,006,376 B2 | 2/2006 | Kozicki |
| 7,081,641 B2 | 7/2006 | Kawasaki et al. |
| 7,101,728 B2 | 9/2006 | Kozicki et al. |
| 7,142,450 B2 | 11/2006 | Kozicki et al. |
| 7,145,794 B2 | 12/2006 | Kozicki |
| 7,169,635 B2 | 1/2007 | Kozicki |
| 7,180,104 B2 | 2/2007 | Kozicki |
| 7,201,821 B2 | 4/2007 | Hoshino et al. |
| 7,227,169 B2 | 6/2007 | Kozicki |
| 7,288,781 B2 | 10/2007 | Kozicki |
| 7,294,875 B2 | 11/2007 | Kozicki |
| 7,372,065 B2 | 5/2008 | Kozicki et al. |
| 7,380,128 B2 | 5/2008 | Bourrieres et al. |
| 7,385,219 B2 | 6/2008 | Kozicki et al. |
| 7,402,847 B2 | 7/2008 | Kozicki et al. |
| 7,405,967 B2 | 7/2008 | Kozicki et al. |
| 7,438,237 B2 | 10/2008 | Bourrieres et al. |
| 7,560,722 B2 | 7/2009 | Kozicki |
| 7,647,279 B2 | 1/2010 | Bourrieres et al. |
| 7,675,766 B2 | 3/2010 | Kozicki |
| 7,726,708 B2 | 6/2010 | Bourrieres et al. |
| 7,728,322 B2 | 6/2010 | Kozicki |
| 7,763,158 B2 | 7/2010 | Kozicki |
| 7,783,081 B2 | 8/2010 | Roques et al. |
| 7,815,117 B2 | 10/2010 | Tuschel et al. |
| 7,852,451 B2 | 12/2010 | Kim et al. |
| 8,039,870 B2 | 10/2011 | Burke et al. |
| 8,056,822 B2 | 11/2011 | Bourrieres et al. |
| 8,292,986 B2 | 10/2012 | Goia et al. |
| 8,345,910 B2 | 1/2013 | Chae et al. |
| 8,396,265 B1 | 3/2013 | Ross et al. |
| 8,576,070 B2 | 11/2013 | Bourrieres et al. |
| 8,742,531 B2 | 6/2014 | Kozicki |
| 8,999,819 B2 | 4/2015 | Kozicki et al. |
| 9,582,751 B2 | 2/2017 | Bourrieres et al. |
| 9,773,141 B2 | 9/2017 | Kozicki |
| 9,790,538 B2 | 10/2017 | Berrada et al. |
| 9,836,633 B2 | 12/2017 | Kozicki |
| 10,074,000 B2 | 9/2018 | Kozicki |
| 10,223,567 B2 | 3/2019 | Kozicki |
| 10,282,480 B2 | 5/2019 | Murrah et al. |
| 10,467,447 B1 | 11/2019 | Kozicki |
| 10,503,890 B2 | 12/2019 | Cambou et al. |
| 10,558,172 B2 | 2/2020 | Kozicki |
| 10,810,731 B2 | 10/2020 | Kozicki |
| 11,170,190 B2 | 11/2021 | Kozicki |
| 2001/0027922 A1 | 10/2001 | Chen et al. |
| 2002/0004632 A1 | 1/2002 | Lindquist et al. |
| 2002/0040852 A1* | 4/2002 | Barber .............. H01L 21/288 257/E21.174 |
| 2002/0055239 A1 | 5/2002 | Tuominen et al. |
| 2002/0126889 A1 | 9/2002 | Pikler et al. |
| 2002/0168820 A1 | 11/2002 | Kozicki et al. |
| 2004/0026917 A1 | 2/2004 | Bauer et al. |
| 2004/0072423 A1* | 4/2004 | Jorne ................ C25D 17/001 257/E21.585 |
| 2004/0104802 A1 | 6/2004 | Becker et al. |
| 2004/0104807 A1 | 6/2004 | Ko |
| 2004/0174257 A1 | 9/2004 | Kuhns et al. |
| 2005/0275831 A1 | 12/2005 | Silver |
| 2006/0029855 A1 | 2/2006 | Ji et al. |
| 2006/0086901 A1 | 4/2006 | Price et al. |
| 2006/0146515 A1 | 7/2006 | Hwang et al. |
| 2006/0159329 A1 | 7/2006 | Joshi et al. |
| 2007/0090918 A1 | 4/2007 | Engstrom et al. |
| 2007/0132998 A1 | 6/2007 | Tang et al. |
| 2007/0275230 A1 | 11/2007 | Murphy et al. |
| 2008/0027651 A1 | 1/2008 | Sieknneier et al. |
| 2008/0179405 A1 | 7/2008 | Benderly |
| 2008/0219503 A1 | 9/2008 | Di Venuto et al. |
| 2008/0260941 A1 | 10/2008 | Jin |
| 2009/0017284 A1 | 1/2009 | Dionigi et al. |
| 2009/0186756 A1 | 7/2009 | Cheng et al. |
| 2009/0242416 A1 | 10/2009 | Yun et al. |
| 2009/0258241 A1 | 10/2009 | Shiraishi et al. |
| 2009/0323959 A1 | 12/2009 | Hara |
| 2010/0007896 A1 | 1/2010 | Fishbaine |
| 2010/0164219 A1 | 7/2010 | Jeacock et al. |
| 2010/0193365 A1 | 8/2010 | Lopatin et al. |
| 2010/0216026 A1 | 8/2010 | Lopatin et al. |
| 2010/0284585 A1 | 11/2010 | Wang et al. |
| 2011/0000970 A1 | 1/2011 | Abraham |
| 2011/0143811 A1 | 6/2011 | Rodriguez |
| 2011/0205542 A1 | 8/2011 | Pendell Jones et al. |
| 2011/0253789 A1 | 10/2011 | Thiele et al. |
| 2011/0254117 A1 | 10/2011 | Kozicki |
| 2012/0080528 A1 | 4/2012 | Crowley |
| 2012/0169647 A1 | 7/2012 | Kuo et al. |
| 2012/0323787 A1 | 12/2012 | Nelsen |
| 2013/0022238 A1 | 1/2013 | Wood et al. |
| 2013/0026645 A1 | 1/2013 | Mohammed et al. |
| 2013/0088555 A1 | 4/2013 | Hanina |
| 2013/0088583 A1 | 4/2013 | Northcott et al. |
| 2013/0117078 A1 | 5/2013 | Weik et al. |
| 2013/0127959 A1 | 5/2013 | Hanina |
| 2013/0220413 A1 | 8/2013 | Kozicki et al. |
| 2013/0228821 A1* | 9/2013 | Kozicki .............. H01L 23/4827 257/459 |
| 2014/0086474 A1 | 3/2014 | Le |
| 2014/0105449 A1 | 4/2014 | Caton et al. |
| 2014/0119612 A1 | 5/2014 | Wang et al. |
| 2014/0169647 A1 | 6/2014 | Ruszczycki et al. |
| 2014/0185891 A1 | 7/2014 | Schoennneyer et al. |
| 2014/0297545 A1 | 10/2014 | Prasad et al. |
| 2014/0316044 A1 | 10/2014 | Wang et al. |
| 2014/0379529 A1 | 12/2014 | Agasti et al. |
| 2015/0084984 A1 | 3/2015 | Tomii et al. |
| 2015/0194545 A1 | 7/2015 | Kozicki et al. |
| 2015/0247252 A1 | 9/2015 | Montemor et al. |
| 2016/0012310 A1* | 1/2016 | Kozicki .............. G06F 16/9554 382/218 |
| 2016/0034758 A1 | 2/2016 | Kozicki |
| 2016/0078617 A1 | 3/2016 | Kozicki |
| 2016/0086001 A1 | 3/2016 | Kozicki |
| 2016/0259970 A1 | 9/2016 | Wee et al. |
| 2017/0185880 A1 | 6/2017 | Lin et al. |
| 2017/0246323 A1 | 8/2017 | Tomalia et al. |
| 2018/0008967 A1 | 1/2018 | Yu et al. |
| 2018/0051176 A1 | 2/2018 | Okada et al. |
| 2018/0088059 A1 | 3/2018 | Kozicki |
| 2018/0286035 A1 | 10/2018 | Kozicki |
| 2019/0197265 A1 | 6/2019 | Kozicki |

(56) References Cited

U.S. PATENT DOCUMENTS

| | | | |
|---|---|---|---|
| 2019/0218707 | A1 | 7/2019 | Pollini et al. |
| 2019/0262897 | A1 | 8/2019 | Zhao et al. |
| 2019/0354733 | A1 | 11/2019 | Kozicki |
| 2020/0117882 | A1 | 4/2020 | Kozicki |
| 2020/0130066 | A1 | 4/2020 | Zhao et al. |
| 2020/0272797 | A1 | 8/2020 | Kozicki |
| 2021/0157888 | A1 | 5/2021 | Kozicki |
| 2021/0295497 | A1 | 9/2021 | Kozicki |
| 2022/0027620 | A1 | 1/2022 | Kozicki |

FOREIGN PATENT DOCUMENTS

| | | |
|---|---|---|
| EP | 2973234 | 1/2016 |
| EP | 2998949 | 3/2016 |
| EP | 2998950 | 3/2016 |
| EP | 3002744 | 4/2016 |
| EP | 3007155 | 4/2016 |
| FR | 2890666 | 3/2007 |
| JP | 2010-090443 | 4/2010 |
| WO | WO 1997/048032 A2 | 12/1997 |
| WO | WO 1997/048032 A3 | 12/1997 |
| WO | WO 1998/048319 | 10/1998 |
| WO | WO 2000/048196 | 8/2000 |
| WO | WO 2007/102988 | 9/2007 |
| WO | WO 2010/008567 | 1/2010 |
| WO | WO 2010/077622 | 7/2010 |
| WO | WO 2012/065076 | 5/2012 |
| WO | WO 2012/065083 | 5/2012 |
| WO | WO 2012/177845 | 12/2012 |
| WO | WO 2014/165047 | 10/2014 |
| WO | WO 2014/165148 | 10/2014 |
| WO | WO 2016/073910 | 5/2016 |
| WO | WO 2017/062425 | 4/2017 |
| WO | WO 2019/126656 | 6/2019 |
| WO | WO 2019/210129 | 10/2019 |
| WO | WO 2020/117950 | 6/2020 |

OTHER PUBLICATIONS

Al-Sid-Cheikh et al., "Synthesis and characterization of [110mAg]-nanoparticles with application to whole-body autoradiography of aquatic organisms," Appl. Radiat. Isot., 2011, 69(10):1415-1421.
Bae et al., "Biomimetic Microfingerprints for Anti-Counterfeiting Strategies,"Advanced Materials, 2015, 27(12):2083-2089.
Balakrishnan et al., "A low power non-volatile memory element based on copper in deposited silicon oxide," 7th Annual Non-Volatile Memory Technology Symposium, 2006, pp. 104-110.
Baloukas, "Thin Film-Based Optically Variable Security Devices: From Passive to Active," Ecole polytechnique de Montreal, Aug. 1, 2012, pp. 1-249, XP055876886.
Berthier et al., "Multiscaled polarization effects in Suneve coronata (Lepidoptera) and other insects: application to anti-counterfeiting of banknotes," Applied Physics A, Oct. 11, 2006, 86:123-130.
BonAppetit.com [online], "The 15 Most Common Counterfeit Foods—and How to Identify Them," Feb. 4, 2014, retrieved on Dec. 13, 2021, retrieved from URL <https://www.bonappetit.com/entertaining-style/trends-news/slideshow/counterfeit-foods>, 12 pages.
Butera, "Fractal Electrodes," NNIN REU Research Accomplishments, 2012:176-177.
CDC.gov [online], "Multistate Outbreak of E. coli O157:H7 Infections Linked to Romaine Lettuce (Final Update)," Jun. 28, 2018, retrieved Dec. 13, 2021, retrieved from URL <https://www.cdc.gov/ecoli/2018/o157h7-04-18/index.html>, 10 pages.
Chaudhuri et al., "Texture Segmentation Using Fractal Dimension," IEEE Transactions on Pattern Analysis and Machine Intelligence, 1995, 17(1):72-77.
Chen et al., "Polarization-based method for object surface orientation information in passive millimeter-wave imaging," IEEE Photonics Journal, Febmary 2016, 8(1):1-12.
Chen et al., "Ultrasonically Assisted Synthesis of 3D Hierarchical Silver Microstructures," The Journal of Physical Chemistry C, 2009, 113(44):19258-19262.

Cheung et al., "Implementation issues in RFID-based anti-counterfeiting systems," Computers in Industry, Apr. 7, 2011, 62(7):708-718.
Chi et al., "Consistency penalized graph matching for image-based identification of dendritic patterns," IEEE Access, Jun. 26, 2020, 8:11863-118637.
Devadas et al.," Design and Implementation of PUF-Based "Unclonable" RFID ICs for Anti-Counterfeiting and Security Applications," 2008 IEEE International Conference on RFID, Apr. 16-17, 2008:58-64.
Ding et al., "Tuning the surface enhanced Raman scattering activity of gold nanocubes by silver coating," Applied Surface Science, 2015, 357:487-492.
Edwards et al., "Reconfigurable Memnstive Device Technologies," Proceedings of the IEEE, Jul. 2015, 103(7):1004-1033.
EurekAlert.org [online], "Stealth Mark licenses ORNL invisible micro-taggant for anticounterfeiting applications," Jun. 25, 2018, retrieved on Dec. 13, 2021, retrieved from URL <https://www.eurekalert.org/pub_releases/2018-06/drnl-sml062518.php>, 3 pages.
European Examination Report for Application No. 14778653.7, dated Nov. 4, 2016, 8 pages.
European Examination Report for Application No. 15188964.9, dated Mar. 8, 2016, 7 pages.
European Examination Report for Application No. 15188965.6, dated Jul. 12, 2016, 6 pages.
European Examination Report for Application No. 15188967.2, dated Jul. 28, 2016, 12 pages.
European Examination Report for Application No. 15188968.0, dated Jul. 28, 2016, 12 pages.
European Search Report for Application No. 14778653.7, dated Oct. 21, 2016, 10 pages.
European Search Report for Application No. 14779748.4, dated Dec. 12, 2016, 10 pages.
European Search Report for Application No. 14779748.4, dated Dec. 23, 2016, 8 pages.
European Search Report for Application No. 15188964.9, dated Feb. 17, 2016, 8 pages.
European Search Report for Application No. 15188965.6, dated Feb. 24, 2016, 7 pages.
European Search Report for Application No. 15188967.2, dated Mar. 8, 2016, 6 pages.
European Search Report for Application No. 15188968.0, dated Mar. 8, 2016, 9 pages.
European Search Report for Application No. 18204507.0, dated Mar. 7, 2019, 22 pages.
Extended European Search Report in International Appln. No. 18817477.5, dated Feb. 16, 2021, 9 pages.
Fleury et al., "Rapid electroplating of insulators," Nature, Apr. 2002, 416(6882):716.
Forbes.com [online], "The 2008 Milk Scandal Revisited," Jul. 16, 2014, retrieved on Dec. 13, 2021, retrieved from URL <https://www.forbes.com/sites/yanzhonghuang/2014/07/16/the-2008-milk-scandal-revisited/#2786cbee4105>, 3 pages.
Han et al., "Lithographically Encoded Polymer Microtaggant Using High-Capacity and Error-Correctable QR Code for Anti-Counterfeiting of Drugs," Advanced Materials, 2012, 24(44):5924-5929.
Han et al., "Magnetic Silver Hybrid Nanoparticles for Surface-Enhanced Resonance Raman Spectroscopic Detection and Decontamination of Small Toxic Molecules," ACS Nano, 2013, 7(4):3212-3220.
Heer et al., "Single-chip Microelectronic System to Interface with Living Cells," Biosensors and Bioelectronics, 2007, 22(11):2546-3553.
Hu et al., "Photonic anti-counterfeiting using structural colors derived from magnetic-responsive photonic crystals with double photonic bandgap heterostructures," Journal of Material Chemicals, 2012, 22:11048-11053.
IBM.com [online], "Pairing AI with Optical Scanning for Real-World Product Authentication," May 23, 2018, retrieved on Dec. 13, 2021, retrieved from URL <https://www.ibm.com/blogs/research/2018/05/ai-authentication-verifier/>, 8 pages.

(56) References Cited

OTHER PUBLICATIONS

Ilic et al., "Synchronized Secrets Approach for RFID-enabled Anti-Counterfeiting," Internet of Things Conference 2008 (Zurich, CH), retrieved on May 15, 2013, dated Jan. 1, 2008, retrieved from the URL: <http://www.stop-project.eu/Portals/1/publications/080128_Demo_IoT_v07.pdf>, 4 pages.

ImageJ.net [online], "Analyze Skelton," available on or before Jan. 17, 2018, via Internet Archive: Wayback Machine URL <https://web.archive.org/web/20180117122909/https://imagej.net/AnalyzeSkeleton>, retrieved on Feb. 28, 2020, from URL <https://imagej.net/AnalyzeSkeleton>, 14 pages.

Imai et al., "Anisotropic Growth of Silver Crystals with Ethylenediamine Tetraacetate and Formation of Planar and Stacked Wires," Crystal Growth & Design, 2005, 5(3):1073-1077.

Independent.co.uk [online], "Cracking down on China's dangerous fake food sector," Aug. 7, 2017, retrieved on Dec. 13, 2021, retrieved from URL <https://www.independent.co.uk/news/world/asia/china-fake-food-sector-unlicensed-products-knock-offs-supply-chain-contamination-public-health-a7880341.html>, 7 pages.

Je et al., "In situ tuning of a MEMS microphone using electrodeposited nanostructures," Journal of Micromechanics and Microengineering, 2009, 19 035015, 8 pages.

Jordan et al., "Identifying Counterfeit Medicines with Industry-Suitable Technologies," Pharmaceutical Engineering, Official Magazine of ISPE, Anti-Counterfeiting Technologies, May/Jun. 2012, 32(3), 7 pages.

Katsuki et al., "High Magnetic Field Effect on the Growth of 3-Dimensional Silver Dendrites," Chemistiy Letters, 2002, 31(12):1186-1187.

Koushanfar, "Provably Secure Active IC Metering Techniques for Piracy Avoidance and Digital Rights Management," IEEE Transactions on Information Forensics and Security, Feb. 1, 2012, 7(1):51-63.

Kozicki et al., "Electrodeposit formation in solid electrolytes," 7th Annual Non-Volatile Memory Technology Symposium, 2006:111-115.

Kozicki et al., "Flow regulation in microchannels via electrical alteration of surface properties," Superlattices and Microstructures, Sep. 1, 2003, 34(3-6):467-473.

Kozicki et al., "Information storage using nanoscale electrodeposition of metal in solid electrolytes," Superlattices and Microstructures, Sep. 1, 2003, 34(3-6):459-465.

Kozicki et al., "Nanoscale effects in devices based on chalcogenide solid solutions," Superlattices and Microstructures, 2000, 27(5/6):485-488.

Kozicki et al., "Nanostrcuture of solid electrolytes and surface electrodeposits," PhysicaE, 2003, 19(1-2):161-166.

Kuo et al., "Formation of Silver Nanoparticles under Structured Amino Groups in Pseudo-dendritic Poly(allylamine) Derivatives," J. Phys. Chem. B, 2003, 107(41):11267-11272.

Lee et al., "Preparation of Silver Dendritic Nanoparticles Using Sodium Polyacrylate in Aqueous Solution," Chemistry Letters, Jan. 2004, 33(2):118-119.

Lee et al., "Universal process-inert encoding architecture for polymer microparticles," Nature Materials, 2014, 13(5):524.

Lee, "Micro-Technology for Anti-Counterfeiting," Microelectronic Engineering, 2000, 53:513-516.

Levin et al., "Senate Armed Services Committee Releases Report on Counterfeit Electronic Parts," May 21, 2012, retrieved on Feb. 28, 2020, retrieved from URL <https://www.armed-services.senate.gov/press-releases/senate-armed-services-committee-releases-report-on-counterfeit-electronic-parts>, 4 pages.

Liu et al., "Controllable Synthesis of Silver Dendrites via an Interplay of Chemical Diffusion and Reaction," Industrial & Engineering Chemistiy Research, 2016, 55(30):8319-8326.

Liu et al., "Fabrication of Infrared Left-Handed Metamaterials via Double Template-Assisted Electrochemical Deposition," Advanced Materials, Jun. 4, 2008, vol. 20, No. 11, pp. 2050-2054, XP055876818.

Liu et al., "Multiple Pass-Band Optical Left-Handed Metamaterials Based on Random Dendritic Cells," Advanced Functional Materials, 2008, 18(21):3523-3528.

Lowe, "Object recognition from local scale-invariant features," Proceedings of the International Conference on Computer Vision 2, Sep. 1999:1150-1157.

Mitkova et al., "Morphology of electrochemically grown silver deposits on silver-saturated Ge—Se thin films," Journal of Non-Crystalline Solids, 2003, 326&327:425-429.

NaturalNews.com [online], "Sticky PLU Labels on Fruit Provide Useful Health Information," Jul. 28, 2008, retrieved on Dec. 13, 2021, retrieved from URL <http://www.naturalnews.com/023711_fruit_labels_health.html>, 10 pages.

Ngo et al., "Paper surfaces functionalized by nanoparticles," Advances in Colloid and Interface Science, 2011, 163(1):23-38.

Nguyen-yhi et al., "On the interest of synchrotron X-ray imaging for the study of solidification in metallic alloys," Comptes Rendus-Physique, Jan. 20, 2012, 13(3):237-245.

Nocke et al., "Dielectrophoretic alignment of polymer compounds for thermal sensing," Sensors and Actuators A: Physical, Nov. 1, 2009, 156(1):164-170.

Office action in U.S. Appl. No. 14/775,413, dated Apr. 19, 2016, 15 pages.

Office action in U.S. Appl. No. 14/775,413, dated Feb. 16, 2017, 21 pages.

Office action in U.S. Appl. No. 14/775,447, dated Jan. 11, 2017, 8 pages.

Office action in U.S. Appl. No. 14/857,655, dated Nov. 10, 2016, 7 pages.

Organization for Economic Co-operation and Development, "Global trade in fake goods worth nearly half a trillion dollars a year—OECD & EUIPO," 2016, retrieved Mar. 5, 2020, retrieved from URL <https://www.oecd.org/industry/global-trade-in-fake-goods-worth-nearly-half-a-trillion-dollars-a-year.htm>, 2 pages.

PCT International Preliminary Report on Patentability in International Appln. No. PCT/US2014/024233, dated Sep. 24, 2015, 9 pages.

PCT International Preliminary Report on Patentability in International Appln. No. PCT/US2014/024557, dated Sep. 24, 2015, 9 pages.

PCT International Preliminary Report on Patentability in International Appln. No. PCT/US2015/059561, dated May 18, 2017, 8 pages.

PCT International Preliminary Report on Patentability in International Appln. No. PCT/US2018/038087, dated Dec. 26, 2019, 7 pages.

PCT International Search Report and Written Opinion in International Appln. No. PCT/US2014/024233, dated Jul. 11, 2014, 12 pages.

PCT International Search Report and Written Opinion in International Appln. No. PCT/US2014/024557, dated Jul. 11, 2014, 13 pages.

PCT International Search Report and Written Opinion in International Appln. No. PCT/US2015/059561, dated Feb. 25, 2016, 12 pages.

PCT International Search Report and Written Opinion in International Appln. No. PCT/US2018/038087, dated Oct. 18, 2018, 10 pages.

PCT International Search Report and Written Opinion in International Appln. No. PCT/US2019/057680, dated Jan. 14, 2020, 7 pages.

PCT International Search Report and Written Opinion in International Appln. No. PCT/US2019/064496, dated Jan. 30, 2020, 12 pages.

PopularMechanics.com, "The Pentagon Uses Plant DNA to Catch Counterfeit Parts," Nov. 21, 2016, retrieved on Dec. 13, 2021, retrieved from URL <https://www.popularmechanics.com/military/research/a23988/plant-dna-pentagon-counterfeit/>, 6 pages.

Psilodimitrakopoulos et al., "Quantitative Imaging of Microtubule Alteration as an Early Marker of Axonal Degeneration after Ischemia in Neurons," Biophysics Journal, Mar. 2013, 104(5):968-975.

ResearchandMarkets.com [online], "Global Brand Counterfeiting Report, 2018," available on or before May 28, 2019, via Internet

(56) References Cited

OTHER PUBLICATIONS

Archive: Wayback Machine URL <https://web.archive.org/web/20190528093101/https://www.researchandmarkets.com/research/7j712n/global_brand?w=4>, retrieved on Feb. 28, 2020, URL <https://www.researchandmarkets.com/research/7j712n/global_brand?w=4>, 12 pages.

Riley, "How Barcodes Can Help Fight Food Fraud," Food Engineering, Sep. 2017, retrieved from URL <https://www.foodengineeringmag.com/articles/96990-how-barcodes-can-help-fight-food-fraud>, 3 pages.

Roysam et al., "The Farsight Project: Associative 4D/5D Image Analysis methods for Quantifying Complex and Dynamic Biological Microenvironments," Microsc Microanal., 2008, 14(Suppl 2):60-61.

Roysam et al., "Farsight: A Divide and Conquer Methodology for Analyzing Complex and Dynamic Biological Microenvironments," Microscopic Image Analysis for Life Science Applications; Atech House Series Bioinformatics & Biomedical imaging, Jan. 1, 2008:115-152.

Ruffato et al., "Design, fabrication and characterization of Computer Generated Holograms for anti-counterfeiting applications using OAM beams as light decoders," Scientific Reports, 2017, 7(18011):1-13.

Russo et al., "Study of Multilevel Programming in Programmable Metallization Cell (PMC) Memory," IEEE Transactions on Electron Devices, May 1, 2009, 56(5):1040-1047.

Sato-Berrú et al., "Silver nanoparticles synthesized by direct photoreduction of metal salts. Application in surface-enhanced Raman spectroscopy," J. Raman Spectrosc., Oct. 20, 2008, 40(4):376-380.

Sawada et al., "Dendritic and Fractal Patterns in Electrolytic Metal Deposits," Physical Review Letters, Mar. 24, 1986, 56(12):1260-1263.

Schindelin et al., "Fiji: an open-source platform for biological-image analysis," Nature Methods, 2012, 9(7):676-682.

Seas.harvard.edu [online], "Technique makes holograms highly efficient, secure," Harvard School of Engineering and Applied Sciences, May 13, 2016, retrieved on Janurary 30, 2017, retrieved from internet: <URL:https://www.seas.harvard.edu/news/2016/05/technique-makes-holograms-highly-efficient-secure>, 4 pages.

Sekerka, "A Stability Function for Explicit Evaluation of the Mullins-Sekerka Interface Stability Criterion," Journal of Applied Physics, 1965, 36(1):264-268.

Serre et al., "A Theory of Object Recognition: Computations and Circuits in the Feedforward Path of the Ventral Stream in Primate Visual Cortex," Computer Science and Artificial Intelligence Laboratory Techmeal Report, MIT-CSAIL-TR-2005-082, Dec. 19, 2005, 131 pages.

Skoric et al., "Experimental Hardware for Coating PUFs and Optical PUFs," In: "Security with Noisy data" by Pim Tuyls et al., Jan. 1, 2007, pp. 256-268.

Smafield et al., "Automatic Dendritic Length Quantification for High Throughput Screening of Mature Neurons," Neuroinformatice, Humana Press Inc., Apr. 9, 2015, 13(4):443-458.

Socol et al., "Suspensive Electrode Formation in Pulsed Sonoelectrochemical Synthesis of Silver Nanoparticles," Langmuir, 2002, 18(12):4736-4740.

Spectrum.ieee.org [online], "How Blockchain Technology Could Track and Trace Food From Farm to Fork," Aug. 29, 2018, retrieved on Dec. 13, 2021, retrieved from URL <http://theinstitute.ieee.org/resources/standards/how-blockchain-technology-could-track-and-trace-food-from-farm-to-fork>, 8 pages.

Tanaka, "Factors leading to ionic migration in lead-free solder," Oct. 1, 2002, retrieved on Feb. 26, 2019, retrieved from URL <https://www.test-navi.com/eng/report/pdf/FactorsLeadingToIonicMigrationInLead-freeSolder.pdf, 9 pages.

TruTags.com [online], "Counterfeiting," available on or before Nov. 2017, retrieved on Dec. 13, 2021, retrieved from URL <https://trutags.com/anti-counterfeiting-solution/>, 6 pages.

Tuyls et al., "Anti-Counterfeiting," Security with Noisy data, Jan. 1, 2007:290-312.

Valehi et al., "A graph matching algorithm for user authentication in data networks using image-based physical unclonable functions," 2017 Computing Conference (London, UK, Jul. 18-20, 2017), 2017:863-870.

Verwer et al., "Descriptive and comparative analysis of geometrical properties of neuronal tree structures," Journal of Neuroscience Methods, Oct. 1, 1986, 18(1-2):179-206.

Wang, et al., "Synthesis of silver dendritic nanostructures protected by tetrathiafulvalene," Chemical Communications, 2002, 12:1300-1301.

WHO.int [online], "Food Safety," 2017, retrieved on Dec. 12, 2021, retrieved from URL <https://www.who.int/news-room/fact-sheets/detail/food-safety>, 7 pages.

Wikipedia.org [online], "Photographic developer," Wikipedia, Oct. 14, 2018, retrieved Mar. 5, 2020, retrieved from URL <https://en.wikipedia.org/w/index.php?title=Photographic_developer&oldid=864027112>, 6 pages.

Witten et al., "Diffusion-Limited Aggregation, a Kinetic Critical Phenomenon," Physical Review Letters, Nov. 9, 1981, 47(19):1400-1403.

Xiao et al., "Novel Ultrasonically Assisted Templated Synthesis of Palladium and Silver Dendritic Nanostructures," Advanced Materials, 2001, 13(24):1887-1891.

Yan et al., "Application of RFID and Internet of Things in Monitoring and Anti-Counterfeiting for Products," 2008 International Seminar on Business and Information Management, IEEE Computer Society, Dec. 19, 2008:392-395.

Zhao et al., "Photochemical synthesis of dendritic silver nanoparticles for anti-counterfeiting," Journal of Materials Chemistiy C, vol. 7, Apr. 29, 2019, pp. 6099-6104.

Zhao et al., "Simple and eco-friendly preparation of silver films coated on copper surface by replacement reaction," Applied Surface Science, 2012, 258(19):7430-7434.

Zhao, "Bottom-up fabrication methods of optical metamaterials," Journal of Materials Chemistry, Jan. 1, 2012, vol. 22, No. 19, p. 9439-9449, XP055876820.

Zhou et al., "A Novel Ultraviolet Irradiation Photoreduction Technique for the Preparation of Single-Crystal Ag Nanorods and Ag Dendrites," Adv. Mater., 1999, 11(10):850-852.

International Search Report and Written Opinion for International Application No. PCT/US2019/029284, dated Aug. 1, 2019, 12 pages.

* cited by examiner

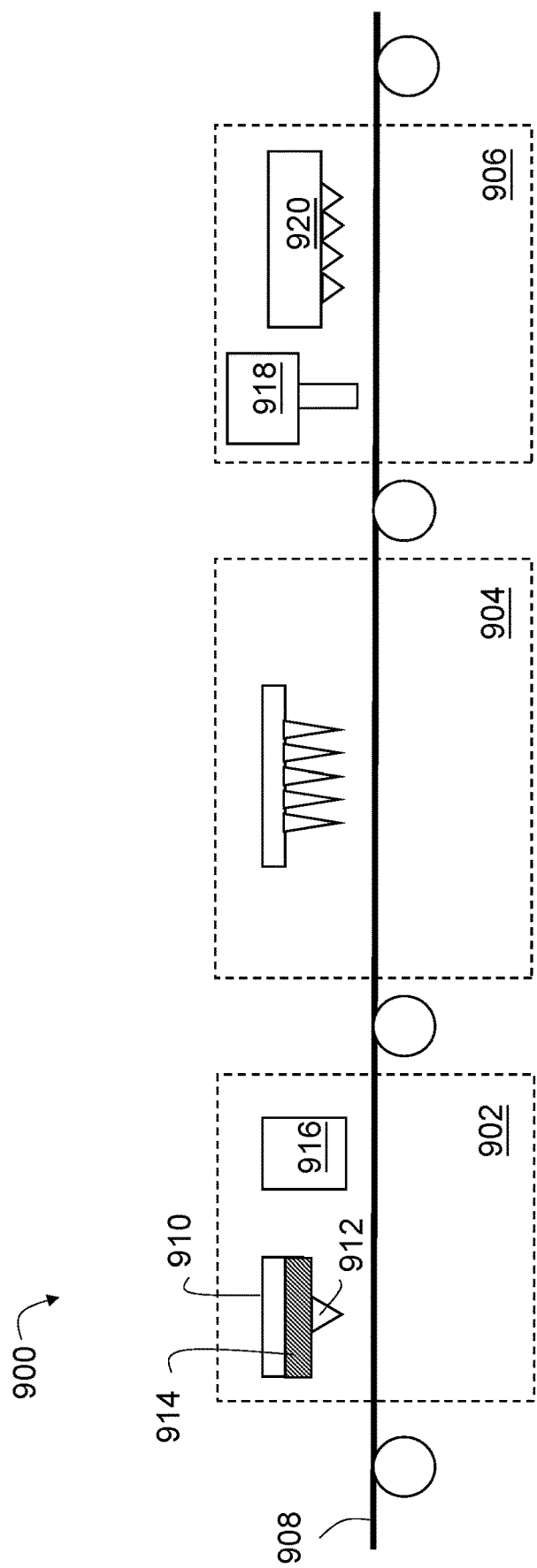

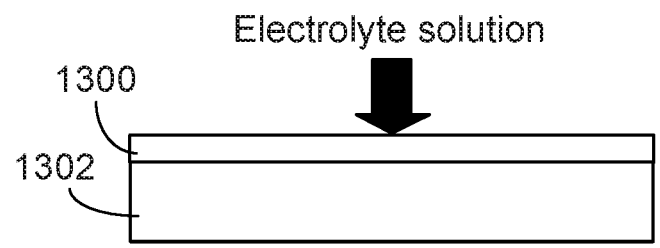
FIG. 13A
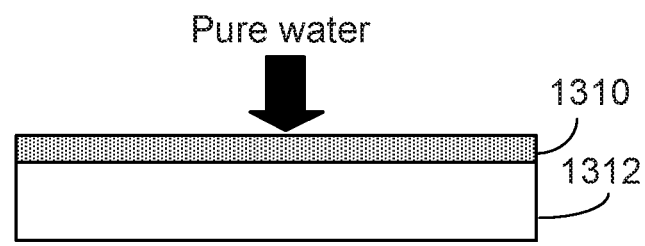
FIG. 13B
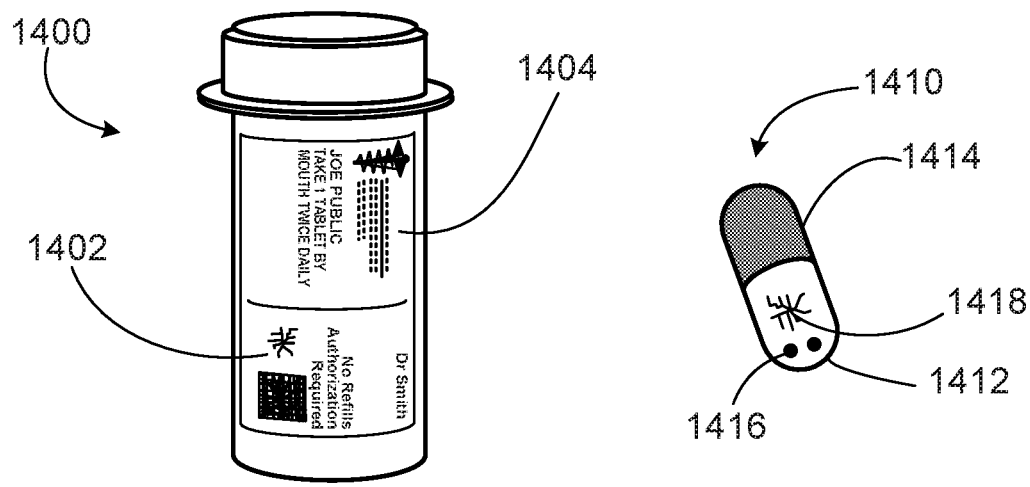
FIG. 14A
FIG. 14B

FABRICATION OF DENDRITIC STRUCTURES AND TAGS

CROSS-REFERENCE TO RELATED APPLICATION

This application is a U.S. National Stage Application under 35 USC § 371 and claims the benefit of International Patent Application No. PCT/US2019/029284 filed on Apr. 26, 2019, which claims the benefit of U.S. Provisional Application No. 62/662,979 filed on Apr. 26, 2018. The disclosures of the foregoing applications are incorporated herein by reference in their entirety.

TECHNICAL FIELD

This disclosure relates to dendritic structures and methods for making dendritic structures.

BACKGROUND

The present disclosure relates generally to the formation and use of dendritic structures. A dendritic structure is a structure that develops with a typical multi-branching, tree-like form. Dendritic patterns are very common in nature and are illustrated by diverse phenomena such as snowflake formation and lightning. Dendritic crystallization forms a natural fractal pattern. A fractal is generally defined as a rough or fragmented geometric shape that can be subdivided into parts, each of which is (at least superficially) a reduced-size copy of the whole, a property called self-similarity. This self-similarity leads to a fine structure at arbitrarily small scales. Because they appear similar (but not identical) at all levels of magnification, fractals are often considered to be infinitely complex. In practice, however, the finest observable levels of structure will be limited by physical and/or chemical constraints.

SUMMARY

This disclosure features methods for the fabrication of dendritic structures. In general, a dendritic metal structure can be formed by the electrodeposition of ions on or in an ion conductor. There are several viable options for the composition of the ion conductor, which can exist as a liquid, solid, or gel. Metals such as silver and copper are particularly appropriate as they are highly mobile in a variety of materials and are readily reduced and oxidized, which makes the electrochemical aspects of the process relatively straightforward.

This disclosure also features dendritic structures that are used for a wide variety of applications. For example, the dendritic structures disclosed herein are used as identification tags for a variety of commercial transactions and security applications. Due to their complex nature and the random processes involved in their formation, dendritic structures are unique and therefore function as "fingerprints," enabling unique tagging and later identification of a wide variety of articles. To permit wide-scale use in commercial environments, the disclosure also features methods for implementing large-volume fabrication of dendritic structures. Further, the disclosure features methods and systems for protecting dendritic structures from tampering once the structures are applied to various articles.

In a first general aspect, the disclosure features methods that include introducing an electrolyte material onto a substrate, into a substrate, or both onto and into a substrate, positioning electrodes on the substrate, and applying electrical potentials to at least some of the electrodes to form one or more dendritic structures on the substrate.

Embodiments of the methods can include any one or more of the following features.

Introducing the electrolyte material can include incorporating the electrolyte material into a body of the substrate. Introducing the electrolyte material can include positioning the substrate in a solution that includes the electrolyte material. Introducing the electrolyte material can include applying at least one of a solid layer and a gel-based layer comprising the electrolyte material to the substrate.

Positioning electrodes on the substrate can include depositing a fluid on the substrate to form the electrodes on the substrate. Positioning electrodes on the substrate can include transferring an image of the electrodes formed on an image carrier to the substrate. The image of the electrodes can be formed from at least one metal material. Positioning electrodes on the substrate can include contacting the substrate with the electrodes.

The methods can include curing the substrate prior to applying the electrical potentials. Curing the substrate can include at least one of heating the substrate and directing a gas to flow over the substrate.

The fluid can be an aqueous solution that includes at least one metal material. The at least one metal material can include silver. The electrodes can be formed of the at least one metal material.

The electrolyte material can include at least one type of metal ion. At least one of the types of metal ions can correspond to the at least one metal material. The electrolyte material can include an aqueous solution of silver ions. The electrolyte material can include an aqueous silver nitrate solution.

Depositing the fluid can include discharging the fluid from a nozzle.

The electrical potentials can be applied to the substrate for a period of between 1.0 seconds and 10 seconds. The dendritic structures can form between pairs of anode and cathode electrodes on the substrate, and the methods can include applying the electrical potentials such that a potential difference between each paired anode and cathode electrodes is between 2.0 volts and 10.0 volts.

The methods can include fixing the substrate after formation of the one or more dendritic structures. Fixing the substrate can include exposing the substrate to a thiosulfate-based fixing solution.

The methods can include oxidizing the one or more dendritic structures formed on the substrate. Oxidizing the one or more dendritic structures can be performed by heating the dendritic structures to a temperature of between 90 degrees C. and 100 degrees C.

The methods can include applying a coating material to the oxidized dendritic structures. The coating material can include at least one material selected from the group consisting of cyanoacrylate, polymethylmethacrylate, polyethylene terephthalate, polysiloxane, silicon dioxide, silicon nitride, polyvinylchloride, and cellulose acetate.

The substrate can be formed from one or more materials selected from the group consisting of synthetic paper materials, polyethylene, polypropylene, polyester, polystyrene, polyamide, polyolefin, acetate, acrylate, vinyl, polyester, and polyethylene terephthalate.

The substrate can include a first structural material and a second adsorbent material. The first structural material can include at least one of a polymeric material and a cloth material. The second adsorbent material can include silica.

The second adsorbent material can be positioned at least partially within a body of the first structural material.

In a second general aspect, forming dendritic structures includes introducing an electrolyte material onto a substrate, into a substrate, or both onto and into a substrate, and applying an electrical potential to at least one pair of electrodes positioned on the substrate to form one or more dendritic structures on the substrate.

In a third general aspect, forming dendritic structures includes contacting a substrate with water, wherein the substrate includes a metal, thereby solubilizing the metal in the water to create an ionically conductive solution, and applying an electrical potential to at least two electrodes positioned on the substrate to form one or more dendritic structures on the substrate.

Implementations of the second and third general aspects can include one or more of the following features in any combination.

Introducing the electrolyte material can include incorporating the electrolyte material into a body of the substrate, contacting the substrate with a solution comprising the electrolyte material, or applying at least one of a solid layer and a gel-based layer comprising the electrolyte material to the substrate.

The first and second general aspects may include positioning the at least one pair of electrodes on the substrate. Positioning the at least one pair of electrodes on the substrate may include contacting the substrate with at least two electrodes. In some cases, positioning the at least one pair of electrodes on the substrate includes depositing a conductive fluid on the substrate or forming metal layers on the substrate, and may further include curing the substrate prior to applying the electrical potential. Curing the substrate may include at least one of heating the substrate and directing a gas to flow over the substrate. Positioning the at least one pair of electrodes on the substrate may include depositing an electrically conductive fluid on the substrate (e.g., by discharging the conductive fluid from a nozzle). The electrically conductive fluid includes at least one metal material. The at least one metal material may include silver. The at least two electrodes can be formed of the at least one metal material.

The electrolyte material typically includes at least one type of metal ion. The at least one of the at least one type of metal ion can correspond to the at least one metal material. The electrolyte material typically includes a metal salt or a metal-containing compound having a solubility in water of at least 1 g/L at 25° C. In some cases, the electrolyte material includes an aqueous solution of silver ions (e.g., an aqueous silver nitrate solution).

The electrical potential is typically applied to the at least one pair of electrodes for a period of between 1 second and 30 seconds. The one or more dendritic structures form between the at least one pair of electrodes on the substrate, and a potential difference between the electrodes in the at least one pair of electrodes is between 2 volts and 20 volts. Some implementations include fixing the substrate after formation of the one or more dendritic structures. Fixing the substrate may include exposing the substrate to a thiosulfate-based fixing solution.

Some implementations include oxidizing the one or more dendritic structures formed on the substrate. Oxidizing the one or more dendritic structures may include heating the dendritic structures to a temperature of between 90 degrees C. and 100 degrees C.

Some implementations include applying a coating material to the one or more dendritic structures. The coating material can include at least one material selected from the group consisting of cyanoacrylate, polymethylmethacrylate, polyethylene terephthalate, polysiloxane, silicon dioxide, silicon nitride, polyvinylchloride, and cellulose acetate.

The substrate typically includes one or more materials selected from the group consisting of synthetic and non-synthetic paper and card materials, polyethylene, polypropylene, polyester, polystyrene, polyamide, polyolefin, acetate, cellulose acetate, acrylate, vinyl, polyester, and polyethylene terephthalate.

In some implementations, the substrate includes a first structural material and a second adsorbent material. The first structural material may include at least one of a polymeric material, a paper material, and a cloth material. The second adsorbent material may include silica. In some cases, the second adsorbent material is positioned at least partially within a body of the first structural material. The second adsorbent material may include a gel, such as gelatin. In some cases, the second adsorbent material includes an electrolyte. The substrate may include a gel. The gel may be coated directly on the substrate. In some cases, the substrate is a capsule configured to contain a pharmaceutical product.

In some implementations, each of the one or more dendritic structure includes a plurality of members extending away from a common point of the dendritic structure to form a stochastically branched arrangement of the members. The one or more dendritic structures can include metal. In some cases, the one or more dendritic structures are, consist of metal, or consist essentially of metal.

Implementations of the second general aspect may include one or more of the following features. The substrate may include a water-permeable gel. The metal may be in the form of a metal salt or a metal-containing compound. The metal salt or the metal-containing compound typically has a solubility in water of at least 1 g/L at 25° C. Each of the one or more dendritic structure includes a plurality of members extending away from a common point of the dendritic structure to form a stochastically branched arrangement of the members.

In a fourth general aspect, a food product or a container includes a dendritic structure affixed to a surface of the food product or the container. In some cases, the container is configured to contain a pharmaceutical product. Each of the one or more dendritic structure includes a plurality of members extending away from a common point of the dendritic structure to form a stochastically branched arrangement of the members.

Embodiments of the methods can also include any of the other features disclosed herein, including features disclosed in connection with different embodiments, in any combination except as expressly stated otherwise.

Certain features, aspects, and steps are disclosed herein in connection with particular embodiments. In general, however, those features, aspects, and steps are not particular to those embodiments, and can be combined with other embodiments and other features, aspects, and steps as desired. Accordingly, while particular embodiments have been described herein for purposes of illustration, it should be appreciated that other combinations of the features, aspects, and steps disclosed herein are also within the scope of the disclosure, and that particular embodiments described herein can also include features, aspects, and steps disclosed in connection with other embodiments.

The entire contents of each of the following are incorporated herein by reference: U.S. Patent Application Publication No. US 2016/0034758; PCT Patent Application Publication No. WO 2014/165148; and PCT Patent Application Publication No. WO 2016/073910.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the subject matter herein, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

FIG. 9A is a schematic diagram showing an example of a system for high-throughput fabrication of dendritic structures and tags.

FIGS. 13A and 13B depict electrochemical activation of gel-based layers.

FIGS. 14A and 14B depict applications for gel-grown dendrites.

Like reference symbols in the various drawings indicate like elements.

DETAILED DESCRIPTION

Dendritic structures appear in a wide variety of natural forms, including, for example, lightning, dielectric breakdown, the flow of rivers, mechanical fractures, and blood vessels. Typically, the particular forms of these dendritic structures are a product of the physical processes that give rise to them and a component of randomness inherent to flow processes. This disclosure introduces dendritic structures by describing certain features thereof and methods for making such structures, including methods for fabricating dendritic structures that are suitable for large-scale manufacturing. Subsequent sections of this disclosure discuss a variety of applications for dendritic structures, including the use of dendritic structures in commercial transactions.

Fabrication of Dendritic Structures

Figure 1:
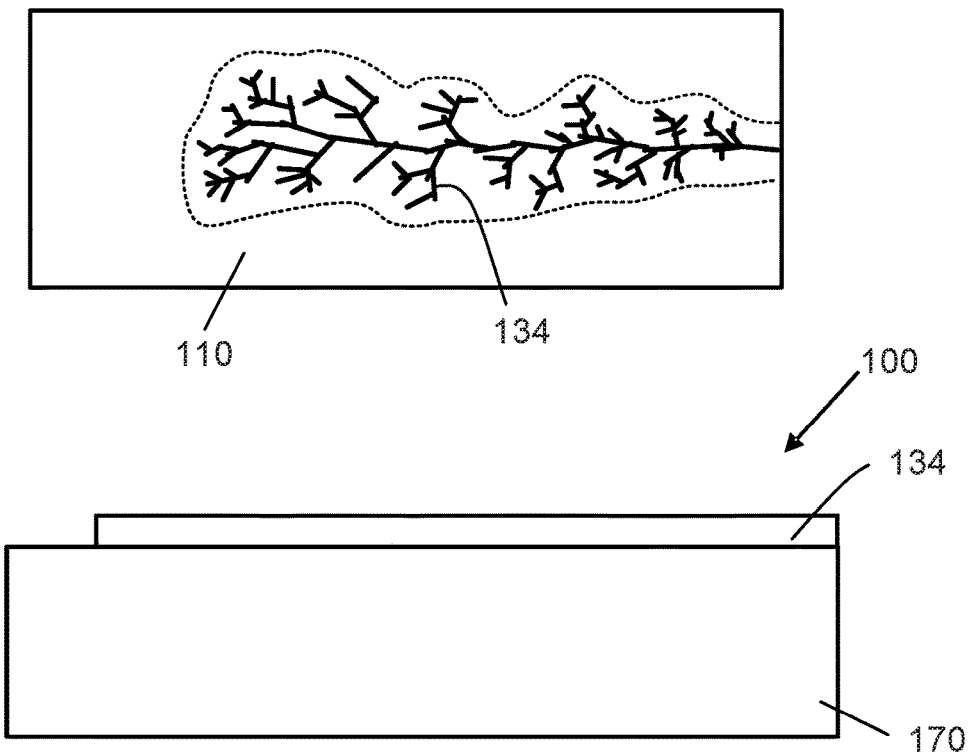
FIG. 1 is a schematic diagram showing an example of a dendritic structure on a substrate.

One example of a dendritic structure is shown in schematic top view in FIG. 1. Dendritic structure 134 is disposed on a substrate 170. Although dendritic structures in nature form by a wide range of physical and chemical processes, metallic dendritic structures have a number of properties that are advantageous for various applications. For example, metallic dendritic structures can be simply formed and "read" electrically and/or optically and/or using other non-destructive measurement methods (for example, using X-ray fluorescence (XRF) methods). Accordingly, dendritic metal structures are useful in many of the applications disclosed herein.

In some implementations, a dendritic structure includes a plurality of members extending away from a common point of the dendritic structure to form a stochastically branched arrangement of members. Due to their multi-branched, stochastically grown structure (as will be described further herein), dendritic metal structures can provide an effectively unique, randomly generated identifier. Moreover, dendritic metal structures can also be made to have "nanoscale" features in their individual conducting elements, which allows them to contain or represent a great deal of information in a relatively small area. Moreover, as will be described in more detail below, because dendritic metal structures can be formed using deposition from a solid electrolyte, the fabrication of such devices can be relatively simple and therefore of low cost. Dendritic metal structures suitable for use in the methods described herein are described generally in U.S. Pat. No. 8,345,910, U.S. Patent Application Publication No. US 2011/0254117, and PCT Patent Application Publications Nos. WO 2012/065076 and WO 2012/065083, the entire contents of each of which are incorporated by reference herein.

Figure 2:
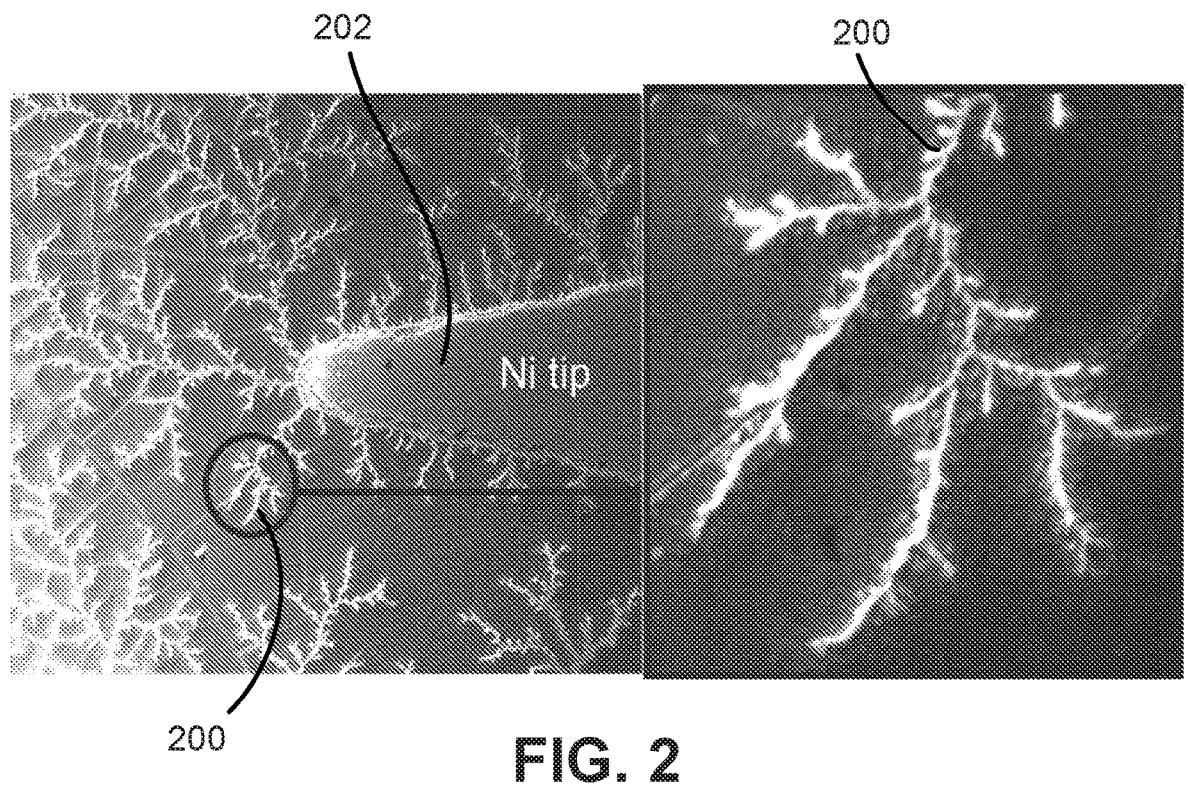
FIG. 2 is a photomicrograph of an example of a dendritic metal structure.
Figure 3:
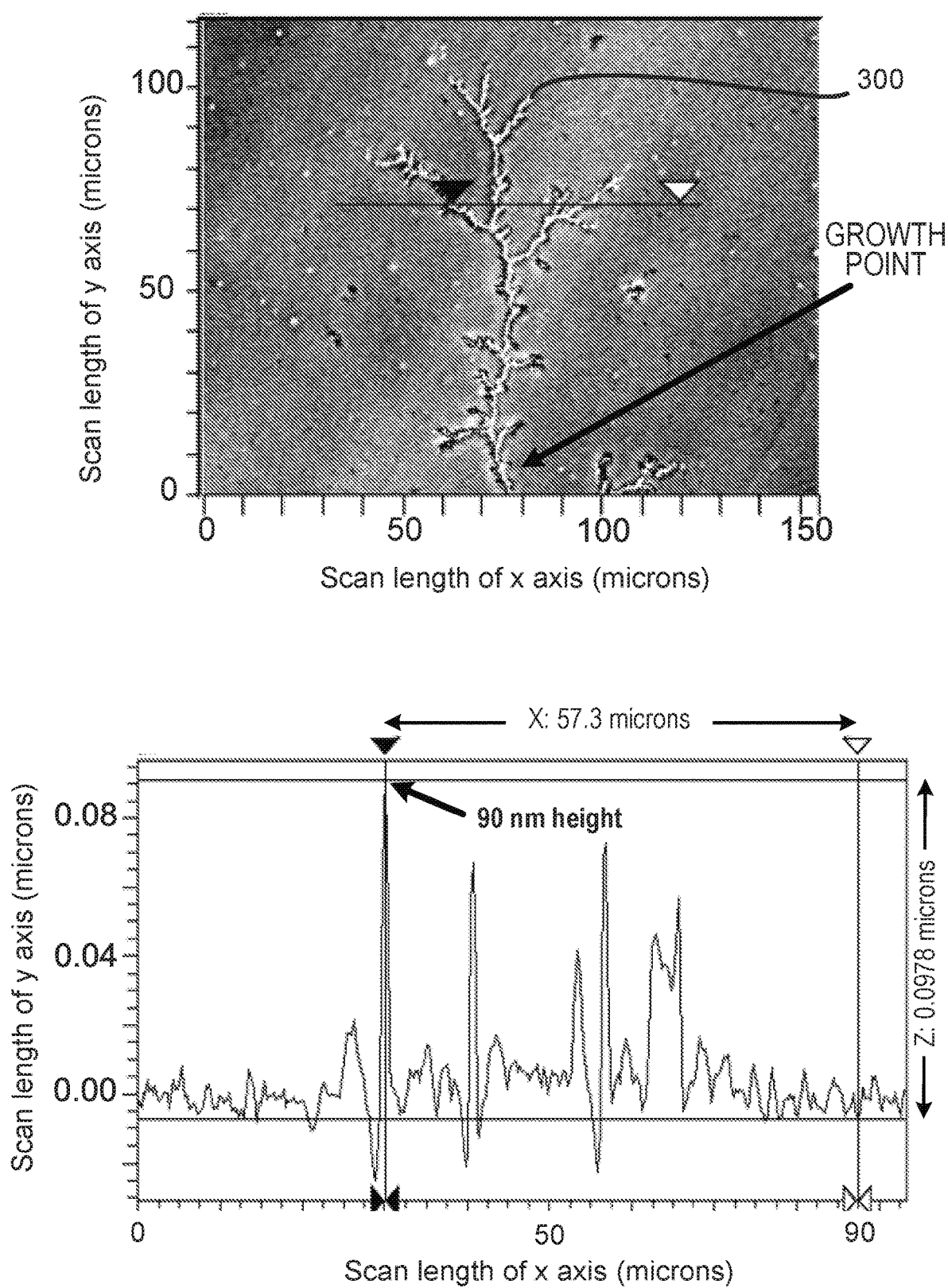
FIG. 3 is a graph showing a profilometry measurement of another example of a dendritic metal structure.

A photomicrograph of an example of a dendritic metal structure 200 is shown in FIG. 2, in which dendritic silver structures are grown from a nickel cathode 202. FIG. 3 is a profilometry measurement of another example of a dendritic metal structure. In general, a dendritic metal structure has a multi-branched structure formed of segments of reduced metallic material. In certain embodiments, dendritic metal structures have an average individual segment width (i.e., in the plane of the dendritic metal structure) of no more than about 300 µm (e.g., no more than about 100 µm, no more than about 10 µm, no more than about 1 µm, or even no more than about 200 nm). In certain embodiments, dendritic metal structures have an average individual segment width of at least about 20 nm.

In some embodiments, dendritic metal structures have an average thickness (i.e., normal to the plane of the dendritic metal structures) of no more than about 100 µm (e.g., no more than about 10 µm, no more than about 5 µm, no more than about 500 nm, no more than about 200 nm, or even no more than about 50 nm). In certain such embodiments, dendritic metal structures have an average thickness of at least about 10 nm.

The areas of dendritic metal structures can range from several mm$^2$ to micro- or even nano-scale dimensions, depending on the method of fabrication and the application for which the structures are used. Dendritic metal structures can include one or a plurality of separately-nucleated branched structures, as described in more detail below.

Dendritic metal structures can be formed from a variety of metallic materials. Metals such as silver and copper can be particularly useful as they are highly mobile in a variety of materials and are readily reduced and oxidized so the electrochemical aspects of the fabrication process are relatively straightforward. Silver is especially appropriate for dendritic structure growth applications due to its nobility and ease of both reduction and oxidation. Accordingly, in certain embodiments, dendritic metal structures are formed from silver. Dendritic metal structures can also be formed, for example, from copper, from zinc, and/or from iron. Dendritic metal structures can also be formed from multiple metals to make duplication of such structures more difficult.

Dendritic metal structures can be formed by electrodeposition in an ion conductor (i.e., an electrolyte) by generating an ion current in the ion conductor and using the flow of ions to build up the dendritic structure in or on the ion conductor via electrochemical processes. The ion conductor can be liquid, gel, or solid, or a combination thereof.

A sustained ion current will only flow through the ion conductor if there is a source of ions at one point and a sink of ions at another. The process of electrodeposition, in which metal cations in the electrolyte are reduced by electrons from a negative electrode (e.g., a cathode), is essentially an ion sink as ions are removed from the electrolyte to become atoms. However, in the absence of an ion source, the reduction of the ions at the cathode occurs at the expense of the electrolyte. The concentration of ions in the solid electrolyte therefore decreases during electrodeposition until the electrode potential equals the applied potential and reduction will cease.

It is therefore desirable in certain embodiments to have an oxidizable positive electrode (e.g., anode)—one which can supply ions into the electrolyte to maintain ion concentration and overall charge neutrality. In the case of a silver (or copper) ion-containing electrolyte, the oxidizable anode can be implemented merely as a solid silver (or copper) member, or a member formed from a compound or alloy containing free metal.

The anode will oxidize when a bias is applied if the oxidation potential of the metal is greater than that of the solid solution. Under steady state conditions, as current flows in the solution, the metal ions will be reduced at the cathode. For the case of silver, the electrode reactions are:

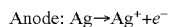

with the bias being supplied by an external power source.

The deposition of Ag metal at the cathode and partial dissolution of the Ag at the anode indicates that fabrication of the dendritic structure is analogous to the reduction-oxidation electrolysis of metal from an aqueous solution, except that when a solid electrolyte is used in fabrication (e.g., rather than a solution of ions), the anions are fixed in position. Accordingly, when a bias is applied across the electrodes, silver ions migrate toward the cathode under the driving force of the applied field and the concentration gradient. At the boundary layer between the electrolyte and the electrodes, a potential difference exists due to the transfer of charge and change of state associated with the electrode reactions. This potential difference, typically in the order of a few hundred millivolts, leads to polarization in the region close to the phase boundary, known as the double layer. Even though the voltage associated with the polarization is small, structures with a long, thin region of solid electrolyte between the electrodes typically require higher voltages to initiate electrodeposition as most of the applied voltage will be dropped across the high resistance electrolyte. For example, the polarization-resistance of a 10 µm² electrode will be around $10^9 \Omega$, but if a 50 nm thick 100 Ω·cm Ag—Ge—Se electrolyte between anode and cathode is 10 µm wide and 100 µm long, the series resistance will be twice this value and so at least 0.75 V is typically used to generate a 0.25 V drop at the cathode to cause electrodeposition.

As in any plating operation, the ions nearest the electron-supplying cathode will theoretically be reduced first. However, in real-world fabrication processes in which the nanoscale roughness of the electrodes is significant and the fields are relatively high, statistical non-uniformities in the ion concentration and in the electrode topography can promote localized deposition or nucleation rather than blanket plating. Even if multiple nuclei are formed, the nuclei with the highest field and best ion supply will be favored for subsequent growth, extending out from the cathode as individual elongated metallic features. The deposition interface continually moves toward the anode, increasing the field and thereby speeding the overall growth rate of the electrodeposit. Without wishing to be bound by theory, it is believed that the addition of new atoms to the growing electrodeposit occurs through a field enhanced diffusion aggregation mechanism.

The electrodeposition of metal on the cathode does not mean that ions entering from the oxidizable anode have to travel the entire length of the structure to replace those that are reduced. For example, in solids, the ions move through the electrolyte by a coordinated motion in which the ion closest to the reduced ion will move to the vacated negative site on the hosting material and those upstream will do likewise, each filling the vacated site of the one downstream, until the last vacated space closest to the anode is filled by the incoming ion. So, in the initial stages of deposition, the electrodeposit is actually made up of reduced ions from the electrolyte itself but since each ion deposited on the growing electrodeposit corresponds to one that has been removed from the metal source, the net effect is a shift of mass from the anode toward the cathode. In general, the growth process in these structures is more complex than a simple plating operation as the deposition interface is moving toward the source of the ions. Since the electrodeposit is physically connected to the cathode, it can supply electrons for subsequent ion reduction, so the growing electrodeposit will harvest ions from the electrolyte, plating them onto its surface to extend itself outwards from the cathode. This has two consequences: the growth interface continually moves out to meet the ions, and the growth closes the gap between the electrodes thereby increasing the field. Both of these help to speed the overall growth rate of the deposit.

Without wishing to be bound by theory, in the most general case, it is believed that the process of deposit formation starts with the nucleation of the new metal atom phase on the cathode and the deposits develop with a structure that generally follows a Volmer-Weber 3-D island growth mechanism. The addition of new atoms to the growing deposit occurs due to a diffusion-limited aggregation (DLA) mechanism, as described for example in T. A. Witten and L. M. Sander, Phys. Rev. Lett. 47: 1400 (1981). In this growth process, an immobile "seed" is fixed on a plane in which particles are randomly moving. Particles that move close enough to the seed in order to be attracted to it attach and form the aggregate. When the aggregate consists of multiple particles, growth proceeds outwards and with greater speed as the new deposits extend to capture more moving particles. Thus, the branches of the core clusters grow faster than the interior regions. The precise morphology depends on parameter such as the potential difference and the concentration of ions in the electrolyte, as described for example in Y. Sawada, A. Dougherty, and J. P. Gollub, *Phys. Rev. Lett.* 56: 1260 (1986).

At low ion concentrations and low fields, the deposition process is determined by the (non-directional) diffusion of metal ions in the electrolyte and the resulting pattern is fractal in nature. For high ion concentrations and high fields as are common in the methods described herein, the moving ions have a strong directional component, and dendritic structure formation occurs. The dendritic structures have a branched morphology, but grow along a preferred axis largely defined by the applied electric field. As an example, FIG. 7 shows dendritic metal structures 700 grown between parallel electrodes (i.e., an anode at the top of the figure and a cathode at the bottom of the figure).

Figure 4:
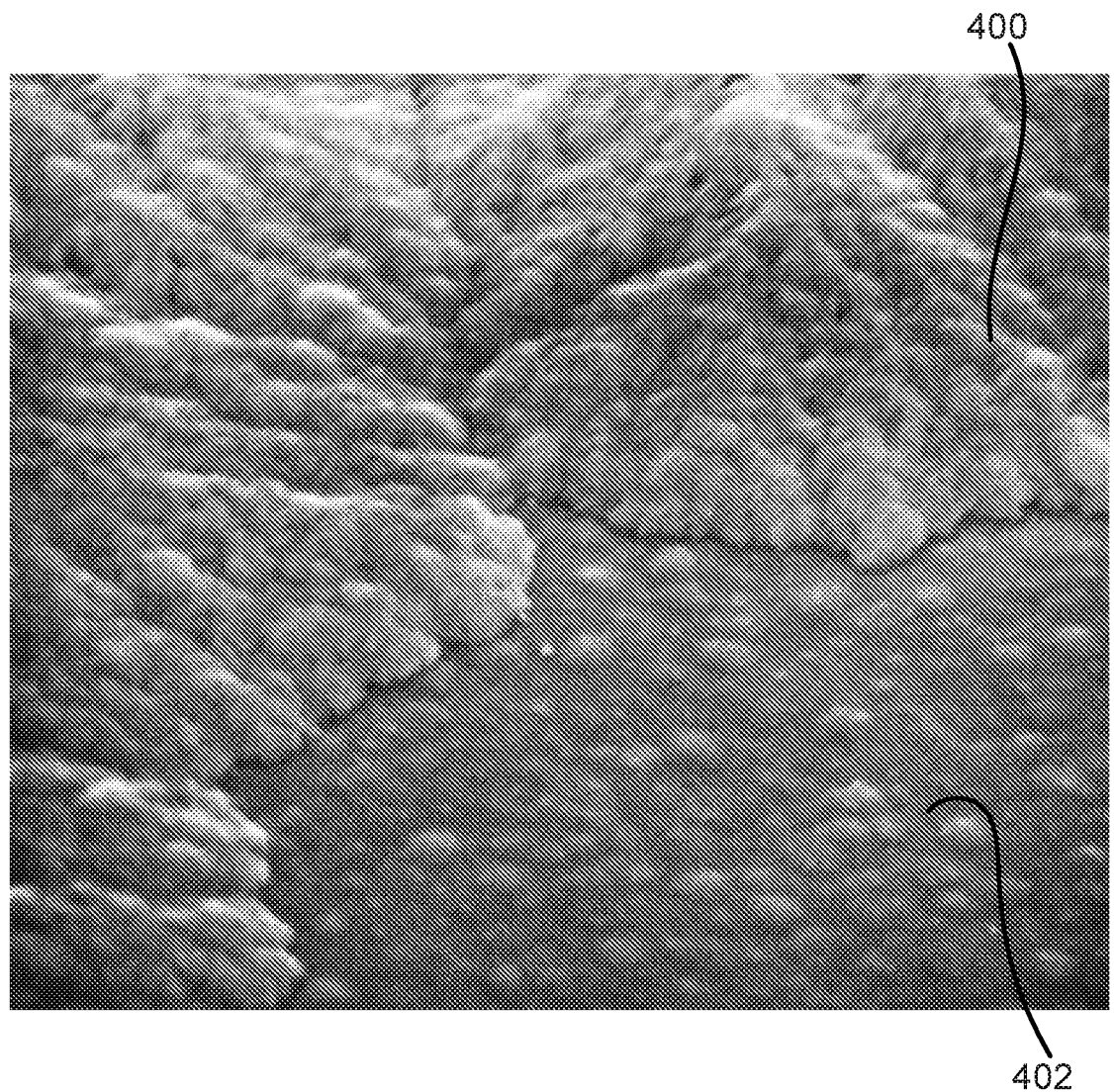
FIG. 4 is a scanning electron micrograph of another example of a dendritic structure.
Figure 7:
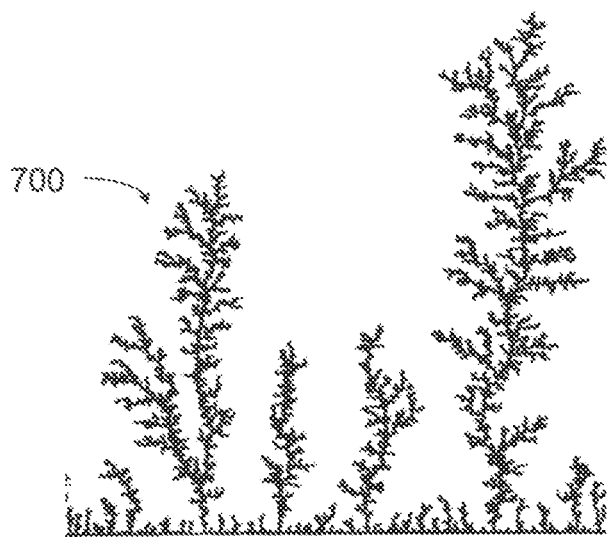
FIG. 7 is an image showing example dendritic structures grown between parallel electrodes.

The complexity of the dendritic form in two dimensions is evident from images such as shown in FIG. 7. The stochastic growth process ensures that the shape of every newly-grown dendritic structure is truly unique. It should be noted, however, that the growth process is generally three dimensional. When a dendritic structure forms inside a solid electrolyte, there are no restrictions on growth direction and the structure will typically branch out like a tree to fill a volume, but even when electrodeposition occurs on the surface of a solid ion conductor, there is still an "upward" component of growth, i.e., in a direction normal to the surface. This occurs because, in addition to the lateral growth across the surface, there is electrodeposition at the interface between the ion conductor and the metal dendrite. This basal deposition pushes the earlier-deposited material upwards, resulting in a nanoscale "mountainous" three-dimensional form. This form is shown in FIG. 4, which is a scanning electron micrograph of the edge of a silver dendritic structure 400 on a silver-doped chalcogenide glass 402. The micro- and nano-scale facets of such 3-D features are once again formed via stochastic processes and introduce yet another layer of complexity (and randomness) to the overall structure.

In some embodiments, dendritic metal structures are formed by methods that include providing an ion conductor and two or more electrodes in contact with the ion conductor, and applying a bias voltage across the electrodes sufficient to grow the dendritic metal structure in or on the ion conductor. Methods for growing dendritic metal structures are described generally in U.S. Pat. No. 8,345,910, U.S. Patent Application Publication No. US 2011/0254117, and PCT Patent Application Publications Nos. WO 2012/065076 and WO 2012/065083.

The stochastic nature of the electrodeposition process leads to randomly-branched and randomly-faceted patterns each time a dendritic structure is grown on a new region of an ion conducting medium. As will be discussed subsequently, as a result of their random and unique nature, these dendritic structures can be used to generate unique identifiers that are useful in a variety of applications, including object identification and tracking, and data encryption. The methods and apparatus used to create these patterns is straightforward and the materials involved can be placed on a variety of substrates, including pliable and/or flexible materials. Examples of device formats and methods for generating dendritic structures are described subsequently in greater detail.

A wide variety of ion conductors can be used, for example, including solid films (e.g., oxides/chalcogenides), gels, and liquids. For certain applications, it can be desirable to use a solid ion conductor. Solid ion conductors are useful due to their mechanical and chemical stability which allows them to be used in the field with minimal encapsulation. Examples of solid ion conductors suitable for use in certain embodiments include "superionic" solid electrolytes (fast ion conductors) and/or other materials such as oxides which have suitable ion mobility.

Dendritic metal structures can be formed by deposition from a solid electrolyte. In certain embodiments, the solid electrolyte includes silver or copper ions, as such materials tend to have high ion mobility and can be less difficult to make than alkali metal solid electrolytes. Silver is also well-suited for electrode growth applications due to its mobility and ease of both reduction and oxidation. In some embodiments, copper-containing solid electrolytes can be used to form dendritic copper structures. For example, crystalline Ag halides, principally AgI, and silver chalcogenides, e.g., $Ag_2S$, $Ag_2Se$, and $Ag_2Te$, and their copper counterparts, can be used as solid electrolytes.

The layer of solid electrolyte can be, for example, a metal-containing chalcogenide glass (i.e., containing oxygen, sulfur, selenium and/or tellurium, although oxide glasses are often treated separately from the others in the literature). Chalcogenide glasses can be formed with a wide range of physical characteristics and can be made using a variety of techniques, such as physical vapor deposition, chemical vapor deposition, spin casting and melt quenching. The tellurides exhibit the most metallic character in their bonding and are the "weakest" glasses as they can crystallize very readily (hence their use in so-called phase change technologies such as re-writable CDs and DVDs) and the others exhibit an increasing glass transition temperature going further up Group VI of the periodic table, with oxides having the highest thermal stability. Stable binary glasses can, for example, include a Group IV or Group V element, such as germanium or arsenic, with a wide range of atomic ratios possible. The bandgaps of the chalcogenide glasses range from about 1-3 eV for telluride, selenide and sulfide glasses, to 5-10 eV for the oxide glasses. The non-oxide glasses are typically more flexible than oxide glasses, but more rigid than organic polymers; other physical properties follow the same trend. Such structural flexibility can result in the formation of voids through which ions can readily move from one equilibrium position to another. It can also allow chalcogenides glasses to be used with flexible substrates.

In some embodiments, a solid electrolyte formed of Ag-doped $Ge_{30}S_{70}$ is used for dendritic structure fabrication. In other embodiments, different materials can be used as the solid electrolyte. For example, silver- or copper-doped oxide glasses such as $SiO_2$ or transition metal oxides can be used in harsher operating environments. Such glasses can withstand higher processing temperatures, are more resistant to mechanical abrasion and chemical damage, and can provide higher transmission over the visible wavelength range than the higher chalcogenide glasses, but may provide slower dendritic structure growth due to lower ion mobility.

In certain embodiments, the chalcogenide glass is a germanium chalcogenide glass. Germanium chalcogenides have relatively low coulombic energies and relatively low activation energies for ion transport. Germanium chalcogenides are desirably glassy in nature; ion conductivity can often be greater in glassy materials than in the corresponding crystalline materials. Of course, crystalline or semi-crystalline materials can also be used. Germanium chalcogenides also tend to be relatively soft materials, making them suitable for use in certain methods in which the dendritic metal structure is formed, annealed or otherwise moved to the interface between the solid electrolyte and the electrically active structure, as described in more detail below. Germanium chalcogenides are also relatively flexible, and can be used on flexible devices. Accordingly, in some embodiments, devices that include the fabricated dendritic structure(s) are flexible. These mechanical properties of the germanium chalcogenides also help avoid cracking during thermal expansion and mechanical stress during use.

In certain embodiments, the solid electrolyte includes a solid solution of $As_xS_{1-x}$—Ag, $Ge_xSe_{1-x}$—Ag, $Ge_xS_{1-x}$—Ag, $As_xS_{1-x}$—Cu, $Ge_xSe_{1-x}$—Cu, $Ge_xS_{1-x}$—Cu, where x ranges from about 0.1 to about 0.5, other chalcogenide materials incorporating silver, copper, zinc, iron, combinations of these materials, Ag- and Cu-doped transition metal oxides, Ag- and Cu-doped silicon or germanium oxides, and the like. Photodissolution techniques can be used to load metal and/or metal ions into the solid electrolyte.

In some embodiments, the solid electrolyte includes a germanium-selenide glass with about 10 to about 50 atomic percent silver diffused in the glass (e.g., $Ag_{33}Ge_{20}Se_{47}$). Such materials can be formed using evaporation. Additional solid electrolyte materials and methods of forming them are discussed in U.S. Pat. No. 6,635,914, the entire contents of which are incorporated herein by reference.

As one example of the fabrication of the solid electrolyte, a 50 nm layer of $Ge_{0.20-0.40}Se_{0.80-0.60}$ is first deposited onto the surface of an electrically active structure, and the Ge—Se layer is covered with about 20 nm of silver. The silver is dissolved into the Ge—Se glass by exposing the silver to a light source having a wavelength of about 405 nm and a power density of about 5 mW/cm² for about ten minutes. Any excess silver is then removed using a $Fe(NO_3)_3$ solution. The solid electrolyte material is then patterned and etched using reactive ion etching (RIE) (e.g., $CF_4+O_2$) or wet etching (e.g., using NaOH:IPA:DI).

The addition of metallic elements such as silver or copper to a chalcogenide glass transforms it into an electrolyte, as silver and copper atoms can form mobile cations within the chalcogenide glass material. The ions are associated with the non-bridging chalcogen atoms but the bonds formed are relatively long. As with any coulombic attraction, the coulombic energy is proportional to the inverse of the cation-anion distance, so long bonds lead to reduced attractive forces between the charged species. The Ge-chalcogenide glasses are therefore among the electrolytes with the lowest coulombic energies. Thermal vibrations will allow partial dissociation, which results in a two-step process of defect formation followed by ion migration. The activation energy for this process strongly depends on the distance between the hopping cation and the anion located at the next nearest neighbor as well as the height of the intervening barrier. In addition to having low coulombic energies, the Ge-chalcogenides also have relatively low activation energies for ion transport. In this respect, the existence of channels due to the structure of the electrolyte is critical in the ion transport process. As an example of this effect, the $Ag^+$ conductivity in glassy $AgAsS_2$ is a factor of 100 larger than that in the crystalline counterpart due to the more "open" structure of the non-crystalline material.

The rigidity and bonding character of the oxide electrolytes means that their ion mobility is typically orders of magnitude lower than that of the Ge-chalcogenides but this also results in higher thermal, chemical, and mechanical stability. Increased stability suggests that Ag- or Cu-doped oxide glasses, such as $SiO_2$ or many of the transition metal oxides (e.g., $WO_3$), may be more suitable for harsher operating environments.

Other electrolyte materials can also be used in the fabrication methods disclosed herein. As suggested above, tellurides (e.g., doped germanium tellurides) can also be used in certain embodiments. In some embodiments, the solid electrolyte is a metal (e.g., copper) doped transition metal oxide.

The solid electrolyte material can have a thickness, for example, in a range of about 1 nm to about 1 μm. In certain embodiments, the layer of solid electrolyte has a thickness in the range of about 5 nm to about 100 nm. In some embodiments, the solid electrolyte has a thickness less than about 10 nm. For example, the solid electrolyte can have a thickness in the range of about 1 nm to about 10 nm. Where the solid electrolyte has low transmissivity at desired wavelengths, use of thinner solid electrolyte layers can improve overall transmission to the electrically-active layer. Such solid electrolyte layers need not be completely continuous on the micro- or nano-scale, as reduced sheet resistance can be achieved even with discontinuous dendritic structures. Moreover, thinner solid electrolyte layers can be more flexible, allowing for increased process and device flexibility. The sold ion conductor may be deposited on the substrate and retained after growth but may also be removed (i.e., before use) to ensure that the dendritic pattern cannot be altered unintentionally after fabrication.

Figure 8:
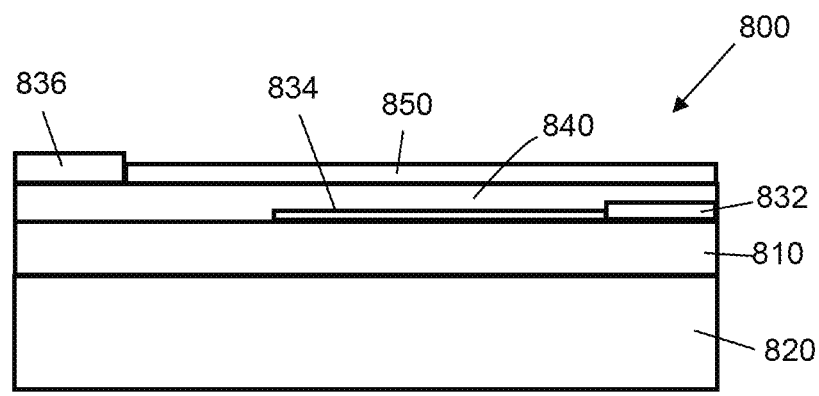
FIG. 8 is a schematic diagram showing an example of a device with a dendritic structure.

In certain embodiments, the dendritic metal structure is disposed at the interface between a substrate and the electrolyte. For example, in the embodiment shown in the schematic side cross-sectional view of FIG. 8, electrical device 800 includes a cathode 832 disposed at the interface between the substrate 810 (on second substrate 820) and a solid electrolyte 840. A sacrificial anode 836 is positioned, for example, on top of the solid electrolyte. To prevent deposition on top of the solid electrolyte, a growth retarding layer 850 (e.g., a hard oxide layer chemically bound to or oxidatively grown from the top of the electrolyte layer) can be formed thereon. A dendritic metal structure 834 can be formed at the interface between the solid electrolyte and the electrically active structure by the application of a bias. In certain embodiments, the solid electrolyte is a relatively soft glass (e.g., a germanium chalcogenide glass such as silver-doped germanium arsenide or selenide), which can deform slightly to allow the dendritic metal structure to grow at the interface. In such embodiments, the dendritic metal structure can have good electrical contact with the electrically active structure, as there is substantially no solid electrolyte disposed therebetween.

In some embodiments, a liquid or gel electrolyte is used for dendritic structure fabrication. Liquid or gel electrolytes are easier to remove after growth and so may be more suitable for tags which only contain the dendritic structure but not the ion conductor in the field. If a liquids or gel electrolyte is to be a permanent (or semi-permanent) part of a fabricated device, the device may include additional layers to contain and protect the electrolyte, as will be discussed in greater detail subsequently.

Figure 5:
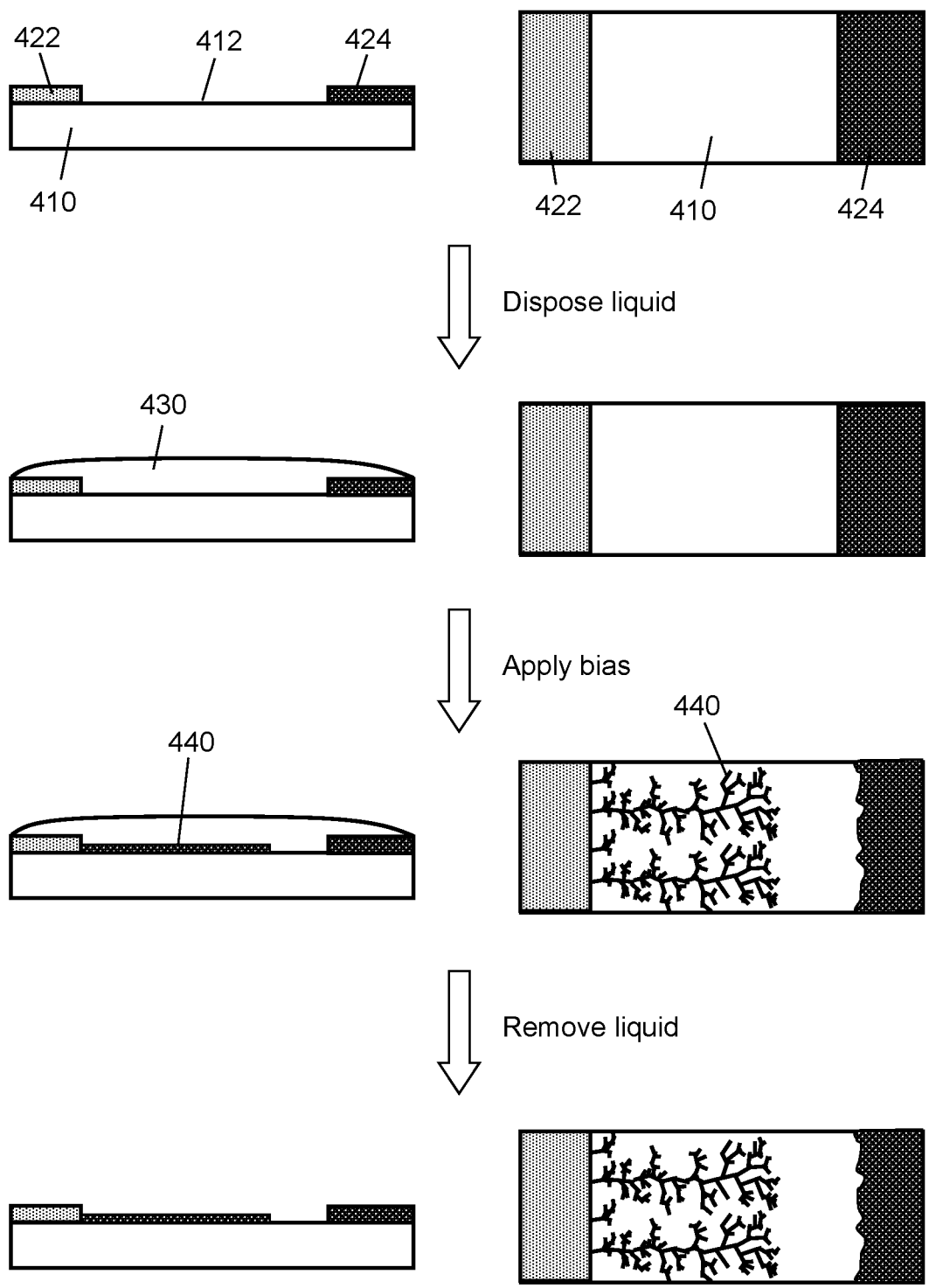
FIG. 5 is a schematic diagram showing an example of a method for fabricating dendritic structures using liquid or gel electrolytes.

FIG. 5 is a schematic diagram showing one embodiment of a method for fabricating dendritic structures using a liquid or gel electrolyte. The method is described herein with respect to a liquid electrolyte, but it should be appreciated that similar steps can be performed in conjunction with the use of a gel electrolyte. A substrate 410 having a surface 412 and a cathode 422 disposed thereon is provided. Also provided is an anode 424 formed from a metal; in this embodiment, the anode is also disposed on surface 412 of the substrate 410. A liquid 430 in which the metal of the anode is at least partially soluble (i.e., in some cationic form) is then disposed on the surface of the substrate. As shown in FIG. 5, in this embodiment, the liquid is simply disposed as a relatively thin film on the surface of the substrate, held in place by surface tension. The liquid is in electrical contact with both the anode 424 and the cathode 422. A bias voltage is applied across the cathode and the anode sufficient to grow the dendritic metal structure 440 extending from the cathode.

Anode 424 and cathode 422 are positioned relative to substrate 410 so that the dendritic metal structure can be electrodeposited. As the dendritic metal structure grows from the cathode, it is disposed on the on the surface of the substrate. The anode can be, for example, also disposed on the surface of the substrate. In such embodiments, the anode can help to direct the growth of the dendrite.

Figure 6:
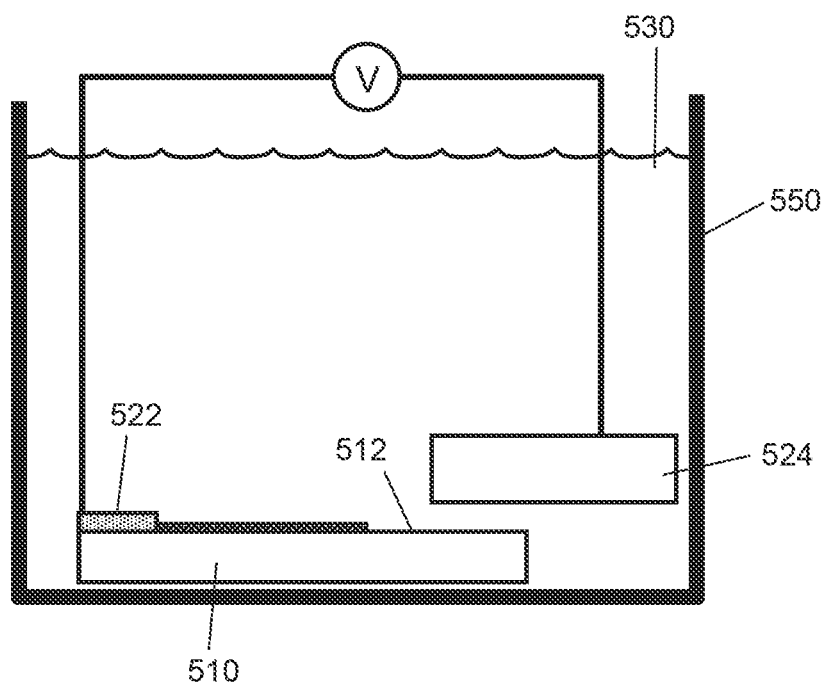
FIG. 6 is a schematic diagram showing an example of a method for fabricating dendritic structures.

In some embodiments, the anode is not disposed on the substrate, but rather is in contact with the liquid. In such embodiments, the anode can, for example, be positioned within 1 cm, or even 5 mm of the surface. For example, FIG. 6 shows an embodiment in which the anode 524 is not disposed on the surface 512 of the substrate 510, but rather is suspended slightly above it. In this example, the liquid 530 is provided in a relatively large volume (i.e., in tank 550, in which the substrate bearing the cathode 522 and the anode are also disposed).

Disposing the electrodes on the substrate surface can have certain advantages. For example, when the electrodes are disposed in such a manner, the electrode contact area and contact resistance can be carefully controlled, ensuring that they are approximately the same for each growth location for dendritic structures. This control can help to ensure that the process of dendritic structure growth is more uniform from one location to another.

However, in certain embodiments, the anode can be placed (i.e., not deposited, such as in the form of a separate piece of metal) on the surface of the substrate, then removed from the surface after deposition. In such embodiments, the anode can help to direct the directionality of growth, as described above, but can easily be removed. In practice, the anode forms part of a voltage source and is contacted with the surface of the substrate during the growth process, and then withdrawn or otherwise removed after the growth process is complete.

In some embodiments, the anode and/or the cathode are placed on the surface of the substrate, but are not deposited thereon. For example, either the anode or the cathode or both can be placed or held in contact with the surface, so as to provide directionality to the growth of the dendritic metal structure, but can be easily removed once growth is complete.

In the process of electrodeposition, metal cations in the liquid are reduced at the cathode. To replace the metal cations in the liquid and allow for continued growth of the dendritic metal structure, the anode can include the same metal as the metal of the dendritic metal structure. As the dendritic metal structure grows by reduction at the cathode, the anode is concomitantly oxidized and dissolved into the liquid, resulting in a net mass transfer from the anode to the growing dendritic metal structure. For example, the anode can be formed of silver, a silver alloy, copper or a copper alloy. When the metal is provided by the anode, the liquid need not have any metal ions dissolved in it when it is disposed on the surface of the substrate. By physically changing the anode material during growth, or by providing an electrical bias in sequence to anodes of differing composition, it is possible to grow a dendritic structure that includes multiple metals either as a mixture or as segments in the structure. Fabricating dendritic structures in this manner makes subsequent replication of the structures (i.e., in a separate growth process) very difficult.

In some embodiments, the anode need not dissolve into the liquid, and the dendritic metal structures can be grown only from the metal initially dissolved into the liquid. For example, the anode can be relatively inert, as described below with respect to the cathode. In such embodiments, a relatively large volume of liquid can be provided in order to supply the desired amount of metal cations.

In certain embodiments, it is possible that the ion conductor is not actually a part of the device structure but is instead incorporated in a "writing" apparatus. In such embodiments, the dendritic structure can be physically transferred to the substrate or otherwise retained on the substrate after growth at the electrolyte-substrate interface. Similarly, in some embodiments, the electrodes are not part of the device and are instead mounted on the apparatus that applies the voltage to the ion conductor, thereby simplifying the device structure.

A transparent layer can be disposed over the dendritic metal structure to protect the electrodeposit from damage and help to prevent duplication of the structure by the use of impression/molding techniques. This layer can be engineered to allow the growth of the dendritic metal structure at the interface between the ion conductor and the protective film or it may be applied after growth. The transparent layer can be, for example, a layer of transparent polymer, or a layer of deposited material such as an oxide or nitride of silicon, titanium or germanium.

In general, substrates used to support the dendritic structure can be rigid or flexible, and a wide range of different materials having different mechanical properties can be used as substrates. Typically, appropriate ion conductors and electrode materials are selected based on the type of substrate that is used.

While a wide range of substrate materials, from insulators to conductors, may be used, in some embodiments an additional barrier layer may be used to prevent interaction between certain substrates and the ion conductor. Thus, the barrier layer is disposed between the substrate and the dendritic metal structure. Accordingly, the barrier layer can be between the ion conductor and the substrate during the electrodeposition operation.

Examples of suitable rigid (or semi-rigid) substrates include glass, hard plastic, metals, and semiconductors. Dendritic structures and devices that include such structures can be formed on integrated circuits (either on the chip itself or outside the package). Examples of flexible substrates include plastic sheets, metal foils, smooth paper, and coated close-weave fabrics.

Electrodes allow the voltage to be applied to the ion conductor to induce the flow of ions and activate the redox processes necessary for electrodeposition. The electrode materials may be deposited and patterned using a variety of methods including sputtering/etching, lift-off, shadow masking, screen printing, and standard (roll-to-roll) printing using conductive inks. In addition, other techniques which will be described subsequently, including inkjet and other digital printing methods, gravure printing, and offset printing, can be used to deposit the electrode materials. A wide range of viable electrode patterns is possible, including parallel, concentric, and multi-contact configurations.

In some embodiments, an anode and a cathode can be formed in contact with a solid electrolyte so that the dendritic metal structure can be electrodeposited. In the process of electrodeposition, metal cations in the electrolyte are reduced at the cathode. To replace the metal cations in the electrolyte and allow for continued growth of the dendritic metal structure, the anode can include the same metal as the metal of the dendritic metal structure and the solid electrolyte. As the dendritic metal structure grows by reduction at the cathode, the anode is concomitantly oxidized and dissolved into the solid electrolyte, resulting in a net mass transfer from the anode to the growing dendritic metal structure. For example, the anode can be formed of silver, a silver alloy, copper or a copper alloy. In other embodiments, the anode need not dissolve into the solid electrolyte, and the dendritic metal structures can be grown only from the metal initially dissolved into the solid electrolyte. For example, the anode can be relatively inert, as described below with respect to the cathode.

In certain embodiments, the cathode can be relatively inert and generally does not dissolve during the electrodeposition operation. For example, the cathode can be formed from an inert material such as aluminum, tungsten, nickel, molybdenum, platinum, gold, chromium, palladium, metal silicides, metal nitrides, and doped silicon.

Of course, in other embodiments, the cathode need not be formed from an inert material. In particular, it should be noted that both the cathode and anode can be formed from reactive materials, and further, in certain embodiments, both the cathode and another can be formed from the same material (for example, both can be formed from copper or from silver). When both electrodes are formed from the metal of the dendritic metal structures, either electrode can act as the anode from which the dendritic metal structures grow, providing additional process flexibility. Appropriate cathode materials can be selected based on the desired electrodeposition conditions. Various configurations of solid electrolyte and electrodes suitable for use in the methods disclosed herein are discussed, for example, in U.S. Pat. No. 6,635,914.

Contacts may be electrically coupled to the anode and/or cathode to facilitate forming electrical contact to the respective electrodes. Contacts can be formed of any conductive material and are preferably formed of a metal such as aluminum, aluminum alloys, tungsten, or copper. Generating the dendritic pattern typically involves the application of a small voltage (e.g., 0.1 to 10 V) to the electrodes in contact with the ion conducting film.

In some embodiments, the fractal dimension of the dendritic structure (i.e., its effective density) can be controlled via the magnitude of the applied voltage; however, the specific shape of the structure is typically random. In certain embodiments, multiple electrodes can be used to generate multiple dendritic forms to fabricate more complex shapes and produce large area dendritic structures. Use of a plurality of dendritic structures in various applications can provide can provide for information redundancy, e.g., in the event that one of the dendritic structures is damaged.

Fabrication of dendritic structures can occur in a variety of contexts and applications. In some embodiments, dendritic structure growth can be performed during manufacture of a tag or device that uses or includes the dendritic structure. In certain embodiments, dendritic structure growth can be performed by user, e.g., during implementation of an application of dendritic structure. In this scenario, the ion conductor can be retained within the device. Conversely, when the dendritic structure is grown during device manufacturing, the fabrication process can be performed with a removable ion conductor. Moreover, provided the electrodes and the ion remain in place, additional growth of the dendritic structure can be performed following manufacture (e.g., during implementation of an application) to deliberately alter an existing dendritic structure.

In some embodiments, when a sufficient bias (e.g., 100 mV or more) is applied across the anode and the cathode, metallic ions (e.g., $Ag^+$) to move from the anode (in this example, made of silver) and/or from metal dissolved in the solid electrolyte toward the cathode. Metallic ions at the cathode are reduced to form the dendritic metal structure, which grows and extends from the cathode out onto the solid electrolyte. The amount of electrodeposited material is determined by factors such as the applied voltage, the nature of the metal, the ion current magnitude and the time during which the current is allowed to flow. The dendritic metal structure can be deposited within or on the layer of solid electrolyte as an increased concentration of reduced metal compared to the concentration of such material in the bulk solid electrolyte material. Electrodeposits can have significant growth parallel to as well as normal to the solid electrolyte surface. The applied bias voltage can typically be, for example, in the range of 200 mV to 20 V, but other bias voltages can also be used.

Dendritic structure growth causes a mass transfer of metal from the solid electrolyte to the growing dendritic structure. For example, when the solid electrolyte has a metallic sheen due to excess metal, the growth process can transfer that metal to the dendritic structure, thereby increasing the apparent transmission of the solid electrolyte. When the solid electrolyte is not replenished with metal (e.g., by a sacrificial electrode), dendritic structure growth can significantly deplete the solid electrolyte of metal. Depletion of metal in the solid electrolyte can also occur when metal dissolves into the solid electrolyte from the anode much more slowly than it is plated onto the dendritic metal structures. In general, the bias voltage applied between the anode and cathode can be reversed to redissolve metal from the dendritic structures, thereby providing a method to more precisely tune the extent of dendritic structure growth.

In certain embodiments, the metal ions can, for example, be provided by the anode. For example, the anode can be formed from the metal dissolved in the solid electrolyte, and the metal of the anode dissolves into the solid electrolyte as the dendritic metal structure is grown.

The following describes one example of fabrication of a dendritic metal structure. On a layer of parylene, $Ge_{30}Se_{70}$ base glass (2400 Å thick) and silver layers (800 Å thick) were thermally evaporated and patterned on the diaphragm. The ratio of $Ge_{30}Se_{70}$ to Ag was approximately 3:1. Immediately after the deposition, photo-dissolution was performed using a 15 min UV exposure to diffuse silver into the $Ge_{30}Se_{70}$ layer to form the solid electrolyte. The anode (silver) and cathode (nickel) were separately evaporated and patterned on the diaphragm. A voltage bias was then applied across the anode and the cathode to grow a dendritic metal structure.

As another fabrication example, a 50 nm layer of $Ge_{0.20-0.40}Se_{0.80-0.60}$ was first deposited onto the surface of a polysilicon material, and the Ge—Se layer was covered with about 20 nm of silver. The silver was dissolved into the Ge—Se glass by exposing the silver to a light source having a wavelength of about 405 nm and a power density of about 5 mW/cm$^2$ for about ten minutes. Any excess silver was then removed using a Fe(NO$_3$)$_3$ solution. The solid electrolyte material was then patterned and etched to provide a desired shape.

A DC bias from 3 to 10 V was applied to electrochemically grow a dendritic silver structure extending out from the tip of the cathode 202, which is shown in FIG. 2. FIG. 3 shows a SEM micrograph of the electrodeposited dendritic silver structure 300. A VEECO NT9800 optical profilometer was used to measure the optical profile in FIG. 3, which shows that the dendritic silver structures had a height on the order of 90 nm.

High-Throughput Fabrication of Dendritic Structures

As discussed above in connection with FIG. 1, the anode(s) used in the fabrication of dendritic structures is/are typically formed from a metal such as copper, silver, or an alloy of copper and/or silver. The cathode(s) is/are typically formed from any one or more of a variety of electrically conductive materials, such as aluminum, tungsten, nickel, molybdenum, platinum, gold, chromium, palladium, metal silicides, metal nitrides, and/or doped silicon. An electrolyte in the form of a liquid can be deposited atop a substrate so that both the cathode and the anode are positioned within the volume of liquid. The liquid can include, for example, water, or another liquid in which metal cations are soluble. More generally, the electrolyte can include a variety of substances, including gels and solid films, in which metal cations are labile.

The cathode and anode are in electrical contact with the liquid by virtue of their positions within the liquid. Accordingly, when an electrical potential difference is applied between the cathode and the anode, a dendritic structure begins to grow in a general direction from the cathode to the anode. The dendritic structure is generally formed from the metal (or one of the metals) that form(s) the anode. During deposition of the dendritic structure, metal cations in the electrolyte are reduced at the cathode, and extend the dendritic structure in the direction of the anode. In some embodiments, metal atoms of the anode are oxidized to form cations during deposition of the dendritic structure. The cations dissolve in the electrolyte (e.g., a liquid) to replace the reduced cations that form the dendritic structure. In certain embodiments, the anode is not oxidized, and the dendritic structure is formed only from metal cations dissolved in the liquid when the liquid is deposited on the substrate.

The morphology of a particular dendritic structure will generally depend upon a number of factors, including the geometry of the cathode and anode, the metal cations that form the dendritic structure, the potential difference applied between the cathode and anode, the ionic current between the cathode and anode, the nature of the electrolyte acting as the ion transport medium, and the deposition time. In general, dendritic structures can be formed from a variety of metals including, but not limited to, silver, copper, zinc, gold, iron, tin, and mixtures thereof.

The fabrication methods described so far can readily be used to fabricate a variety of dendritic structures. However, use of dendritic structures for large volume commercial applications and transactions requires that the structures be fabricated in large numbers. In this section, additional methods are disclosed for fabricating large numbers of dendritic structures.

FIG. 9A is a schematic diagram of a system 900 for high-throughput fabrication of dendritic structures and tags. System 900 includes an electrode print subsystem 902, a dendritic structure growth subsystem 904, and a finishing subsystem 906. A substrate 908 is roll-fed (as shown in FIG. 9A) or fed in sheet form through each of the above subsystems in succession to fabricate the structures. In particular, in the electrode print subsystem 902, anodes and cathodes are applied directly to substrate 908 in a wet printing process, after which the electrode-forming "ink" is cured. Then, in dendritic structure growth subsystem 904, dendritic structures are formed on substrate 908 by applying electrical potentials to the anodes and cathodes deposited in electrode print subsystem 902. Following fabrication, the dendritic structures are stabilized on substrate 908. Next, in finishing subsystem 906, substrate 908 (which now includes one or more dendritic structures) is coated with a protective coating and, optionally, an adhesive material. Substrate 908 is also cut or otherwise separated so that individual structures are available for incorporation into dendritic tags.

Figure 9B:
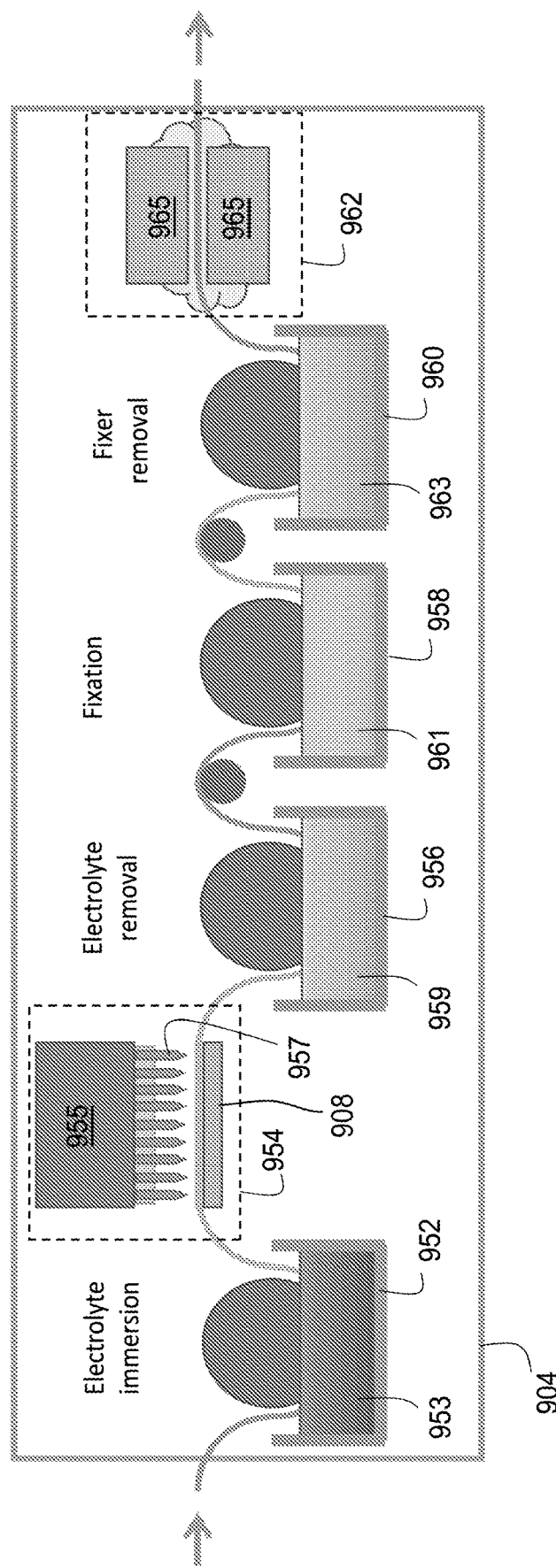
FIG. 9B is a schematic diagram showing one example of a dendritic structure growth subsystem.
Figure 10:
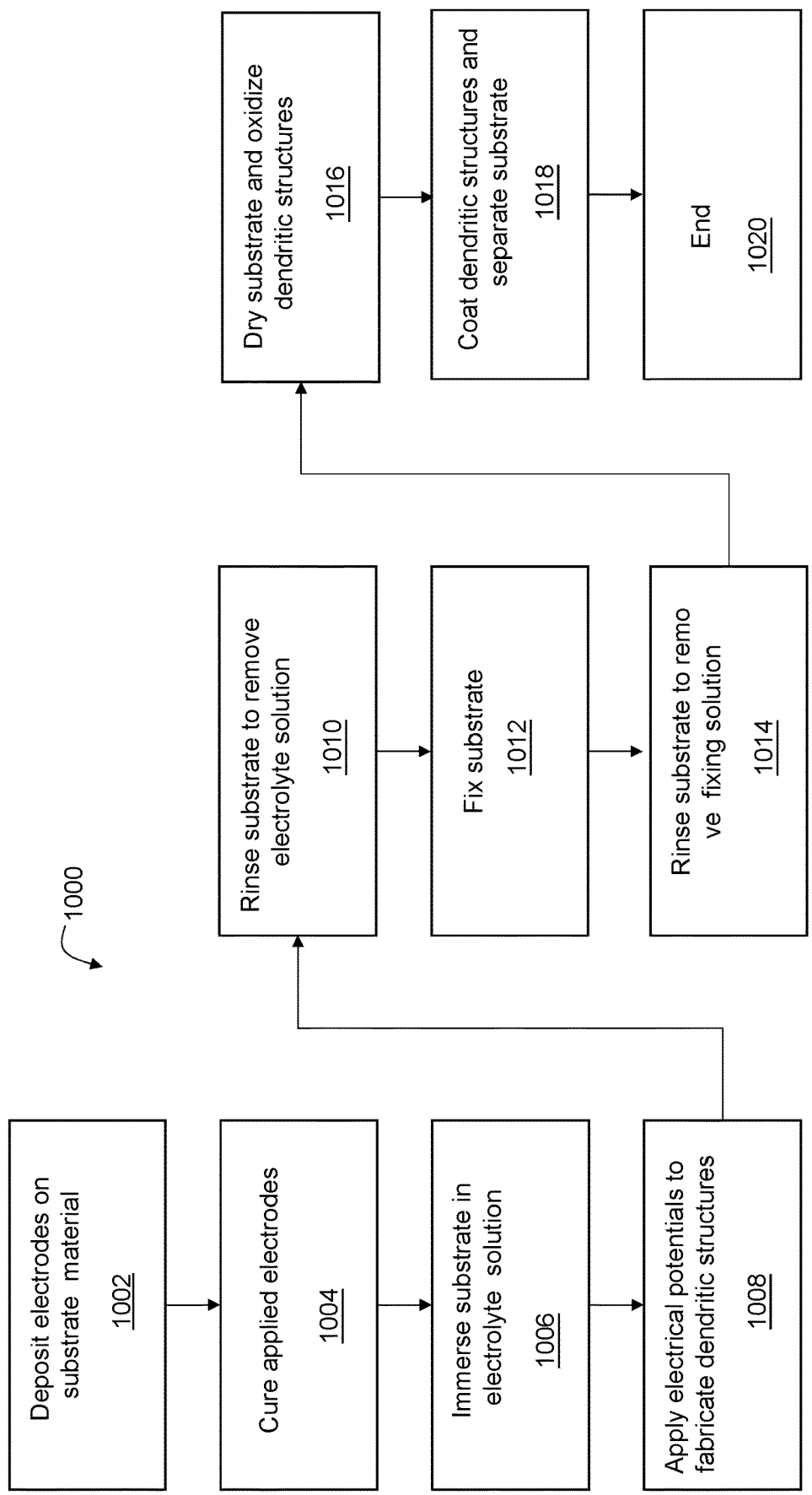
FIG. 10 is a flow chart that includes a series of example steps for fabricating dendritic structures.

FIG. 10 is a flow chart 1000 that includes a series of example steps for fabricating dendritic structures. In a first step 1002, electrodes (i.e., one or more anodes and one or more cathodes) are deposited on substrate 908. A variety of different methods can be used for the deposition. In some embodiments, for example, a fluid (also referred to herein as an "ink") that includes one or more conductive materials can be deposited on substrate 908 to form the electrodes. Referring to electrode print subsystem 902 of FIG. 9A, a reservoir 910 contains the fluid 914, which is discharged through nozzle 912 onto the surface of substrate 908 as the substrate passes through electrode print subsystem 902.

As shown in FIG. 9A, electrode print subsystem 902 implements an inkjet or, more generally, a digital printing process for depositing conducting materials on substrate 908. However, other methods can also be used to deposit conducting materials. In certain embodiments, for example, electrode print subsystem 902 can be a gravure printing subsystem in which in which an image carrier (such as a roller) is imprinted with an image of the electrodes, and contact between the image carrier (e.g., by rolling) and substrate 908 applies the electrodes to substrate 908.

In some embodiments, electrode print subsystem 902 can be an offset printing subsystem in which an image of the electrodes is formed in ink on a printing plate, transferred to an intermediate material surface (such as a rubber or other polymer surface), and then applied to substrate 908 by contacting the intermediate material surface and substrate 908.

A variety of conductive materials can be used in fluid 914. In some embodiments, for example, fluid 914 includes silver (e.g., silver particles suspended in solvent, resin, or aqueous solution), copper (e.g., copper particles suspended in solvent, resin, or aqueous solution), nickel (e.g., nickel particles suspended in solvent, resin, or aqueous solution), carbon (e.g., carbon black or graphite/graphene particles suspended in solvent, resin, or aqueous solution).

It should be noted that, in general, the anode and cathode electrodes can be formed from the same material or from different materials. In some embodiments, for example, both the anode and cathode are formed from silver, from copper, or from any of the other materials discussed previously. Depending upon the nature of electrode print subsystem 902, forming both the anode and cathode from the same material can have certain advantages. Generally, by using the same ink to print both the anode and cathode, the printing process can be considerably simplified, and the speed of the process can be increased accordingly, particularly when using methods such as gravure printing to apply the electrodes to substrate 908.

Various materials can be used to form substrate 908. In certain embodiments, for example, substrate 908 is a synthetic paper material. Other suitable substrate materials include, for example, one or more plastics, such as polyethylene (e.g., polyethylene terephthalate, PET), polypropylene, polyester, polystyrene, polyamide, polyolefin, acetate, acrylate, vinyl, polyester, and Mylar®, and woven and non-woven materials such as linen, silk, microfiber polyester cloth, polyethylene terephthalate (Dacron®), spun-bonded polyolefin (Tyvek®), expanded polytetrafluoroethylene (Goretex®), and a variety of papers.

Returning to FIG. 10, in the next step 1004, the electrodes applied to substrate 908 are cured. Curing ensures that the electrodes are dried and stable in advance of further processing steps that are performed in aqueous solution. Various methods can be used to cure the applied electrodes. For example, in some embodiments, electrode print subsystem 902 (FIG. 9A) includes a curing apparatus 916 that heats substrate 908, that directs a flow of a gas across the surface of substrate 908, or performs both actions, to cure the applied electrodes. The electrodes may also be cured in an oven with an inert ambient, the oven being heated using infra-red heating elements or microwaves, or by passing the substrate between heated plates or rollers.

After the electrodes have cured, substrate 908 with the electrodes applied is directed into dendritic structure growth subsystem 904. Returning to FIG. 10, in the next step 1006, the substrate is immersed in an electrolyte solution to prepare the substrate for the growth of dendritic structures. FIG. 9B is a schematic diagram that shows one example of a dendritic structure growth subsystem 904. Subsystem 904 in FIG. 9B includes an electrolyte immersion bath 952 into which a substrate (not shown) is delivered and maintained for a period of time prior to the growth of dendritic structures on the substrate. While the substrate is in bath 952, the substrate is immersed in electrolyte solution 953.

Various electrolyte solutions can be used in bath 952. In some embodiments, for example, electrolyte solution 953 is a silver nitrate solution. The electrolyte solution may also contain silver chloride, silver lactate, silver sulfamate, silver complexes with hydantoin, and/or silver cyanide. In certain embodiments, electrolyte solution 953 can be a copper-based electrolyte solution that includes aqueous solutions of copper sulfate and/or copper chloride.

The concentration of electrolyte solution 953 can generally be selected as desired, depending upon such factors as the constituents of the solution, the electrical potentials to be applied during dendritic structure growth, and the nature of the substrate material. In certain embodiments, for example, where electrolyte solution 953 is a silver nitrate solution, the concentration of silver ions in the solution can be between 0.05 mol/L and 1.0 mol/L (e.g., between 0.05 mol/L and 0.8 mol/L, between 0.10 mol/L and 0.8 mol/L, between 0.10 mol/L and 0.6 mol/L, between 0.15 mol/L and 0.5 mol/L). Ion concentrations up to 1.0 ml/L are suitable for growth of dendritic structures with applied voltages of between 0.2 V and 10 V. Ion concentrations from 0.005 mol/L to 0.05 mol/L can be used for the growth of dense structures over hundreds of seconds.

In certain embodiments, electrolyte solution 953 is heated during immersion of the substrate in the solution. For example, solution 953 can be maintained at a temperature of between 25 degrees C. and 90 degrees C. (e.g., between 30 degrees C. and 85 degrees C., between 35 degrees C. and 80 degrees C., between 40 degrees C. and 80 degrees C.) during immersion of substrate 908.

Returning to FIG. 10, in the next step 1008, electrical potentials are applied to the electrodes deposited on substrate 908 in step 1002 to initiate growth of dendritic structures on substrate 908. Referring to FIG. 9B, in some embodiments, subunit 954 of dendritic structure growth subsystem 904 includes a plurality of contact electrodes 957 connected to a voltage source 955. Contact electrodes 957 individually contact the electrodes deposited on substrate 908 (i.e., contact electrodes 957 are lowered until they make physical contact with substrate 908). Then, voltage source 955 applies suitable electrical potentials to each of the deposited electrodes on substrate 908 via contact electrodes 957.

As discussed above, dendritic structure growth generally occurs between anode-cathode pairs when an electrical potential difference is applied. In certain embodiments, voltage source 955 applies a potential difference between one or more anode-cathode pairs of deposited electrodes on substrate 908 of between 2.0 V and 10.0 V (e.g., between 2.0 V and 9.0 V, between 3.0 V and 9.0 V, between 4.0 V and 8.0 V).

In general, voltage source 955 applies potential differences between anode-cathode pairs until the growth of dendritic structures on substrate 908 is complete to the extent desired. In certain embodiments, for example, the potential differences are applied by voltage source 955 between pairs of deposited anodes and cathodes for between 1.0 seconds and 10.0 seconds (e.g., between 2.0 seconds and 9.0 seconds, between 3.0 seconds and 8.0 seconds).

Returning to FIG. 10, in a next step 1010 following growth of dendritic structures on substrate 908, the substrate is rinsed to remove electrolyte solution. To implement this step, in certain embodiments dendritic structure growth subsystem 904 includes an electrolyte rinse bath 956. Substrate 908 passes through rinse bath 956 which contains rinsing fluid 959. Rinsing fluid 959 washes remaining electrolyte solution from substrate 908.

Various rinsing fluids can be used to wash away excess electrolyte solution. In some embodiments, for example, rinsing fluid 959 corresponds to water (e.g., deionized water). The rinsing fluids may also be mild acid solutions, mild base solutions, or organic solvents.

In certain embodiments, rinsing of substrate 908 is performed at elevated temperature. For example, as substrate 908 is immersed in rinsing fluid 959, the temperature of rinsing fluid 959 can be maintained between 25 degrees C. and 90 degrees C. (e.g., between 30 degrees C. and 85 degrees C., between 35 degrees C. and 80 degrees C., between 40 degrees C. and 80 degrees C.).

Returning again to FIG. 10, substrate 908 is then fixed in step 1012. Fixation refers to a chemical treatment that halts further activity of any residual electrolyte material on or within substrate 908. To perform this treatment, as shown in FIG. 9B, dendritic structure growth subsystem 904 can include a fixing bath 958. As substrate 908 passes through fixing bath 958, the substrate is exposed to fixing solution 961 contained within the bath. Fixing solution 961 chemically deactivates residual electrolyte material in or on substrate 908.

Various fixing solutions can be used to deactivate electrolyte materials. For example, in certain embodiments, fixing solution 961 is a thiosulfate-based photographic fixing solution. Typical thiosulfates used for fixing include, but are not limited to, sodium thiosulfate and ammonium thiosulfate, sometimes combined with chelating agents such as ethylenediaminetetraacetic acid.

Following fixation of substrate 908, the next step in FIG. 10 is the removal of fixing solution in step 1014 by rising substrate 908. As shown in FIG. 9B, dendritic structure growth subsystem 904 can include a rinsing bath 960 that removes residual fixing solution 961 and any exhausted chemical agents from substrate 908. Rinsing bath 960 operates in a manner similar to bath 956 described above, and can use similar rinsing fluids and temperatures.

Returning to FIG. 10, in the next step 1016, substrate 908 is dried and the dendritic structures grown on the substrate are oxidized. Drying substrate 908 ensures that the substrate 908 is prepared for subsequent mechanical handling operations such as cutting/dicing. The dendritic structures are oxidized to stabilize the surfaces of the structures chemically.

Substrate drying and dendritic structure oxidation can be performed in a variety of ways. In some embodiments, for example, dendritic structure growth subsystem 904 includes a drying/oxidation apparatus 962 featuring heating elements 965. As substrate 908 passes through heating elements 965, the substrate is heated, causing evaporation of residual liquid on or within substrate 908. Further, heating substrate 908 in the presence of atmospheric oxygen initiates oxidation of the dendritic structures formed on substrate 908.

In general, the temperature to which substrate 908 is heated depends upon the nature of substrate 908, the liquid to be removed, and the material(s) from which the dendritic structures are formed. In some embodiments, for example, substrate 908 is heated to a temperature of between 90 degrees C. and 100 degrees C. by heating elements 965. In certain embodiments, substrate 908 is heated to a temperature of between 100 degrees C. and 200 degrees C. to drive off the residual liquid.

Typically, the drying and oxidation processes are performed for a relatively brief period of time. For example, in some embodiments, the drying and oxidation processes are performed in a period of between 10 seconds and 300 seconds (e.g., between 15 seconds and 200 seconds, between 20 seconds and 100 seconds, between 10 seconds and 60 seconds).

After drying and oxidation, in the next step 1018 of flow chart 1000, substrate 908 is delivered to finishing subsystem 906 (FIG. 9A), where coating and cutting of substrate 908 occurs. As shown in FIG. 9A, finishing subsystem 906 can including a coating apparatus 918 for applying one or more coating and/or adhesive materials to substrate 908, and a cutting apparatus 920 for separating substrate 908 into smaller pieces (e.g., each of which contains a dendritic structure).

In general, coating apparatus 918 includes one or more nozzles, heating elements, laminators, spin coating tables, and/or other elements that are used to apply coatings/adhesives to substrate 908. Examples of such coatings are discussed further below.

Cutting apparatus 920 can generally include any one or more of a variety of cutting/dicing elements, including blades/knives, saws, laser cutters, heating elements, any other elements that function to section substrate 908 into smaller pieces.

After substrate 908 has been coated and cut into pieces, the procedure shown in flow chart 1000 ends at step 1020. The pieces of substrate 908, each of which typically includes one or more dendritic structures, can then be used in the subsequent fabrication of dendritic tags for use in a variety of identification, authentication, and tracking applications.

As discussed above, in step 1018, substrate 908 can be coated with various materials which function as protective layers for the dendritic structure(s) grown on the substrate. Examples of such materials include, but are not limited to, cyanoacrylate applied as a low viscosity (high-wicking) liquid and hardened by chemical reaction with water or UV exposure to form a hard acrylic coating, polymethylmethacrylate liquid or vapor hardened by chemical reaction with peroxide or UV exposure to form a hard Lucite® (Perspex®) coating, polyethylene terephthalate, polysiloxane liquid or condensed vapor that is thermally cured to give a silicate coating, silicon dioxide or silicon nitride deposited by the pyrolysis of vapor sources in a chemical vapor deposition reaction to create a highly conformal oxide or nitride film. Polymeric materials such as polyvinylchloride and cellulose acetate may also be applied as a tape, affixed with adhesive, to cover the dendrite.

For use in secure environments, it can be advantageous for dendritic structures supported on substrate 908 to be made more difficult to tamper with following fabrication, and also to be made sufficiently robust to retain their morphologies when exposed to a variety of physical and chemical environments. By rendering the dendritic structures difficult to modify or copy and the tags difficult to remove from articles to which they are applied, duplication or reuse of the tags for counterfeiting purposes is challenging and/or economically infeasible.

To prevent alteration of dendritic structure morphologies and to protect the fabricated structures/tags against degradation in a variety of different environments, the present section discloses various systems and methods for treating fabricated dendritic structures. As discussed above in connection with FIG. 9B, these treatments can be applied to fabricated dendritic structures by finishing subsystem 906.

Figure 11:
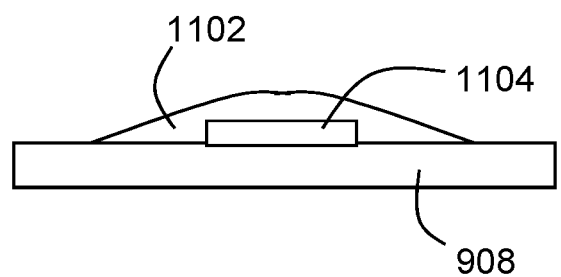
FIG. 11 is a schematic diagram showing an example of a dendritic tag that includes a protective layer encapsulating a dendritic structure.

To protect dendritic structures against environmental degradation, one or more layers of protective materials can be applied to encapsulate the dendritic structure. FIG. 11 shows a schematic diagram of a dendritic tag that includes a substrate 908 and a dendritic structure 1104 formed on the substrate. A protective layer 1102 is applied over dendritic structure 1104 to encapsulate the structure. Although protective layer 1102 in applied to only one surface of substrate 908 in FIG. 11, more generally, protective layer 1102 can be applied to both surfaces of substrate 908 to partially or fully encapsulate both substrate 908 and dendritic structure 1104. Further, although a single protective layer 1102 is applied to the dendritic tag, more generally, one or more protective layers can be applied. Multiple protective layers can include different materials having different properties. For example, in some embodiments, a first protective layer can be applied to mechanical rigidity to the dendritic tag, and a second protective layer can be applied to impart water impermeability to the encapsulated dendritic tag. The following discussion will focus on properties of protective layer 1102 for clarity. However, it should be understood that a variety of different combinations of layers, each having different properties, can be used to protect dendritic tags. In particular, combinations of any number of layers of any of the different materials disclosed herein can be used.

In certain embodiments, protective layer 1102 has a relatively high Mohs hardness number to resist mechanical abrasion of the encapsulated dendritic tag. In some embodiments, for example, the Mohs hardness number of protective layer 1102 is 4 or more (e.g., 5 or more, 6 or more, 7 or more, 8 or more). Further, in some embodiments, protective layer 1102 has relatively high water impermeability and degrades relatively slowly in sunlight. These properties of protective layer 1102 protect the encapsulated dendritic tag against environmental degradation.

In addition, in some embodiments, protective layer 1102 is relatively resistant to a variety of different classes of chemical compounds, including some or all of acids, chlorine-based compounds, bleaches, and detergents. The resistance of protective layer 1102 to these materials further protects encapsulated dendritic tags.

Protective layer 1102 is generally applied to dendritic tags in a manner that preserves the delicate dendritic structure 1104 on each tag. A variety of methods can be used for application of the protective layer. In some embodiments, for example, protective layer 1102 can be vapor deposited using chemical vapor deposition or physical vapor deposition techniques. In certain embodiments, protective layer 1102 can be applied as a low viscosity liquid to dendritic structure 1104 and the upper surface of substrate 908.

Typically, both vapor and liquid deposition techniques are performed in a reduced-pressure environment to ensure that protective layer 1102 fills small gaps between the structural features of dendritic structure 1104. In some embodiments, for example, vapor and/or liquid deposition of protective layer 1102 is performed at an ambient pressure of 100 Torr or less (e.g., 50 Torr or less, 30 Torr or less, 20 Torr or less, 10 Torr or less, 5 Torr or less, 1 Torr or less, 500 mTorr or less, 300 mTorr or less, 100 mTorr or less).

Following deposition of protective layer 1102, in certain embodiments, the protective layer is hardened. Hardening of protective layer 1102 can be performed by physical or chemical techniques. Suitable physical techniques for hardening protective layer 1102 include directing a flow of air onto protective layer 1102, heating the encapsulated dendritic tag to cure protective layer 1102, and/or photocuring protective layer 1102 by exposing protective layer 1102 to radiation, e.g., ultraviolet radiation. Suitable chemical techniques for hardening protective layer 1102 include, for example, exposing protective layer 1102 to chemical cross-linking agents such as formaldehyde.

In general, the material from which protective layer 1902 is formed is chosen for its particular physical and chemical properties to ensure that the dendritic tag it encapsulates is protected from degradation in a variety of different environments. A variety of different materials can be used singly, or in combination, to form protective layer. In some embodiments, protective layer 1102 includes cyanoacrylate, a low-viscosity liquid. A protective layer formed from cyanoacrylate can be hardened by chemical reaction with water and/or by exposure to ultraviolet radiation. Hardening yields a hard acrylic coating over dendritic structure 1104.

In certain embodiments, protective layer 1102 includes polymethylmethacrylate (PMMA), which can be deposited either as a vapor or a liquid onto the dendritic tag, and hardened by chemical reaction with a peroxide material or exposure to ultraviolet radiation. The hardened PMMA forms an acrylic layer that encapsulates dendritic structure 1104.

In some embodiments, protective layer 1102 includes polysiloxane, which can be deposited either as a vapor or a liquid onto the dendritic tag. Hardening of polysiloxane by thermal curing yields a silicate coating that encapsulates dendritic structure 1104.

In certain embodiments, protective layer 1102 includes polyethylene, e.g., polyethylene terephthalate (PET), which can be deposited either as a vapor or liquid onto the dendritic tag (e.g., as a monomer) and hardened by chemical reaction or exposure to heat or ultraviolet radiation. The hardened PET forms a layer than encapsulates dendritic structure 1104.

In some embodiments, protective layer 1102 includes silicon dioxide and/or silicon nitride. These materials can be deposited by pyrolysis of vapor sources in a chemical vapor deposition reaction, yielding a highly conformal oxide and/or nitride film that encapsulates dendritic structure 1104.

Figure 12:
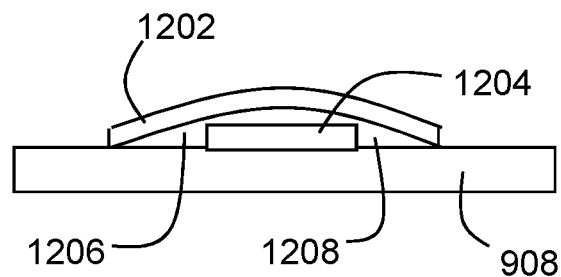
FIG. 12 is a schematic diagram showing another example of a dendritic tag that includes a protective layer applied as a film over a dendritic structure.

FIG. 12 shows a schematic diagram of another dendritic tag featuring a substrate 908 and a dendritic structure 1204 formed thereon. In FIG. 12, the dendritic tag is not encapsulated by a protective layer 1202 deposited from vapor or liquid to form a conformal film on the dendritic structure. Instead, protective layer 1202 formed from a relatively soft, compliant material that is applied as a solid film over the dendritic tag. The technique shown in FIG. 12 is particularly suitable for relatively robust dendritic structures that resist deformation, as the application of protective layer 1202 exerts a downward force on dendritic structure 1204.

Dendritic structure 1204 is sandwiched between protective layer 1202 and substrate 908 in FIG. 12, and may not be fully coated by protective layer 1202 (i.e., not all portions of dendritic structure 1204 may be in contact with protective layer 1202). Voids between protective layer 1202 and dendritic structure 1204, such as voids 1206 and 1208, may trap gases or may enclose volumes in which the pressure is reduced relative to ambient pressure. Following application of protective layer 1202 to the dendritic tag, the protective layer can be hardened using any one or more of the physical and chemical methods disclosed above.

A variety of materials can be used to form the solid protective layer 1202 that is applied to the dendritic tag. Suitable materials include, but are not limited to, acrylic, polycarbonate, PMMA, PVC, and/or glass.

Following application of one or more protective layers, the encapsulated dendritic tag is protected from physical and chemical degradation by the environment, but is accessible for optical measurements and is also electrically (e.g., capacitively) addressable. As such, the dendritic tag can function as an identifier containing information that can be "read" by optical and electrical methods.

In FIGS. 9A, 9B, and 10, which are discussed above as examples of methods for fabricating dendritic structures, electrodes are applied to the surface of substrate 908 and then electrical potentials are applied to the electrodes via contact electrodes 957, which are lowered into contact with substrate 908 and the fabricated electrodes on the substrate surface.

However, other dendritic structure fabrication methods can be used in which electrodes are not fabricated on the surface of substrate 908. In particular, in some embodiments, contact electrodes 957 can be patterned according to a desired arrangement of electrodes on the surface of substrate 908. When contact electrodes 957 are lowered into contact with the substrate, contact occurs at one or more points corresponding to the surface structures and positions of contact electrodes 957, thereby forming electrical contact points on the surface of substrate 908 in the desired pattern. In this manner, patterned dendritic structure growth on substrate 908 can still be achieved, but without performing the electrode and printing steps (e.g., steps 1002 and 1004 in FIG. 10) discussed previously.

In the methods discussed above in connection with FIGS. 9A, 9B, and 10, substrate 908 is immersed in a liquid electrolyte solution 953 in step 1006, or alternatively, a solid or gel-based electrolyte is applied to substrate 908 prior to the application of electrical potentials via contact electrodes 957 to facilitate dendritic structure growth.

However, in certain embodiments, substrate 908 can be formed from one or more materials that incorporate an electrolyte within the structure of substrate 908, such that the immersion step 1006 can be eliminated or performed earlier in the process to "soak" substrate 908 in the electrolyte. In these embodiments, substrate 908 is not immersed in an electrolyte solution, nor is an exterior surface of substrate 908 in contact with a gel-based or solid electrolyte when electrical potentials are applied.

For example, substrate 908 can be formed from certain types of hydrophobic, woven or non-woven, polymeric or cloth materials that are packed with adsorbent, hydrophilic materials such as silica, and that effectively function as "sponges" for electrolytes. When such materials are used to form substrate 908, the procedure shown in FIG. 10 can optionally include a step, performed prior to step 1008, in which an electrolyte material is introduced into substrate 908 by soaking the substrate in an electrolyte solution, by injecting the electrolyte into substrate 908, or by using other methods to drive the electrolyte into the bulk structure of substrate 908. The product of these various optional processes is a substrate 908 that includes electrolyte material incorporated into the body of the substrate, below the substrate surfaces.

Applying electrical potentials to such a substrate 908 (e.g., via electrodes printed on the substrate surface, or directly via a pattern of contact electrodes 957) causes the growth of dendritic structures on the surface of substrate 908, in a manner similar to the methods discussed above. Using a substrate 908 with electrolyte material incorporated into its bulk structure can, in some circumstances, provide certain advantages. In general manufacturing processes, handling and processing such a substrate can be considerably simpler than handling and processing a "dry" substrate with a film of liquid, gel-based, or solid electrolyte deposited on its surface.

It has been observed experimentally that when dendritic structures are grown on a substrate impregnated with electrolyte material, a portion of the dendritic structure may grow into the bulk substrate material. That is, a portion of the dendritic structure growth occurs in a direction orthogonal to the substrate surface, toward the body of the substrate. When the dendritic structure grows at least partially into the substrate, the dendritic structure can essentially become anchored or bound to the substrate in a manner that makes accidental or deliberate removal of the dendritic structure from the substrate without damage to the dendritic structure very difficult. For dendritic structures that are used in a variety of security-related applications, this can be an important aspect to prevent tampering.

It should be noted that the various options and modifications discussed above to the example methods shown in FIGS. 9A, 9B, and 10 can generally be combined with one another, and with any of the steps of FIGS. 9A, 9B, and 10 to implement methods for fabricating dendritic structures. That is, in general, the various steps discussed herein are generally combinable in various ways to fabricate dendritic structures, and except where expressly noted otherwise, method steps disclosed in the context of one embodiment can also be used in other embodiments. In particular, for example, methods for fabricating dendritic structures can include both the use of a substrate 908 with an electrolyte material incorporated into the bulk structure of the substrate, and the application of electrical potentials to the substrate with or without printing electrodes on the surface of substrate 908 before the application of the electrical potentials.

In gel-based implementations, dendritic structures can be grown on a thin layer of a water-permeable gel (e.g., gelatin) on the surface of a substrate (e.g., smooth paper or plastic). Gelatin is low cost, readily available in industrial quantities, and binds as a stable film to a wide variety of rigid and flexible substrates. The permeability of water-permeable gel-based layers to aqueous processing agents allows the water-permeable gel to be electrochemically activated by various methods.

In one implementation, as depicted in FIG. 13A, a water-permeable gel layer 1300 on a substrate 1302 (e.g., paper or plastic) is contacted with an aqueous electrolyte solution. The substrate 1302 having the water-permeable gel layer 1300 may be commercially available, or may be prepared by depositing a layer of water-permeable gel on the substrate. The water-permeable gel layer 1300 may be electrochemically inert. As noted previously, one example of a water-permeable gel is gelatin. Contacting the water-permeable gel layer with an aqueous electrolyte solution may include soaking the substrate in the solution. Suitable examples of aqueous electrolyte solutions include solutions of silver nitrate and copper sulfate, with concentrations in a range of 0.1M to 2M, 0.1M to 1M, 0.1M to 0.5M, or 0.5M to 1M. In another implementation, as depicted in FIG. 13B, a colloid 1310 on a substrate 1312 is contacted with water. The substrate 1312 having the colloid 1310 may be commercially available, or may be prepared by depositing a colloidal mixture of a water-permeable gel and metal salts on the substrate. Suitable examples of metal salts include silver nitrate and copper sulfate and other metal salts having a solubility of at least 1 g/L at 25° C. In some implementations, substrate 1312 has 1 µg to 50 µg of a metal per square centimeter of a substrate. Contacting the colloid 1310 with water may include soaking the substrate 1312 in water, thereby forming an aqueous electrolyte within the water-permeable gel.

For the implementations depicted in FIGS. 13A and 13B, after contacting with the aqueous electrolyte solution or water, respectively, excess liquid may be removed from the surface. Dendritic structures can be grown on the surface of the water-permeable gel by contacting first and second electrodes (e.g., an anode including silver or copper and a cathode including tungsten or other metal, respectively) with the surface or using surface electrodes that have been pre-formed on the substrate (e.g., by screen printing with a conductive ink). Gel-based dendrites can be fabricated in a roll-to-roll process, such as that described with respect to FIGS. 9A and 9B.

In one example, silver dendrites can be grown by soaking commercially available photographic paper having a colloidal layer including gelatin and silver halide crystals. The photographic paper is soaked in a solution including silver nitrate or other metal salt having a solubility of at least 1 g/L at 25° C. and a concentration in a range of 0.1M to 2M, 0.1M to 1M, 0.1M to 0.5M, or 0.5M to 1M. After soaking (e.g., for about 30 min to about 60 min), the excess electrolyte is washed from the photographic paper (e.g., to prevent further reactions). In the case of silver nitrate, a fixer can be used to prevent photo-darkening of residual chemicals. Following growth of dendritic structures, a drying step can be employed. The resulting dendritic structures can be coated with a protective layer (e.g., as described with respect to FIGS. 11A and 11B).

In another example, ILFORD Multigrade IV RC Deluxe variable contrast black & white photo paper (medium weight, 190 gsm resin coated) was used as a substrate having a gelatin layer. The silver halide contained in the gelatin layer does not dissolve readily in solution, and therefore only forms weak electrolytes in water. Thus, for at least this reason, the silver halide in this and other commercially available photo papers are not considered to be suitable for dendrite growth. Electrodes were screen printed onto the gelatin layer using silver ink and allowed to dry for 4 to 5 hours. The substrates were then soaked in silver nitrate solution ($AgNO_3$ dissolved in ultrapure water) with a concentration between 0.1 M and 0.5 M and for 30 to 60 minutes to allow the solution to fully penetrate the gelatin. The substrates were removed from the soaking bath, and excess liquid was removed from the surface, leaving the gelatin saturated with the silver nitrate solution. Generally, compressed air or nitrogen pulses from a nozzle over a period of 10 seconds was adequate to achieve the desired wetness, however, rollers, gentle blading, or blotting may be used to achieve the same effect. After removal of excess liquid, dendrites were grown with an applied bias across the electrodes of 7 to 15 V for 30 to 50 s. The resulting dendritic patterns had well-defined branches. The substrates were allowed to dry to ensure that the dendrites were securely attached to the surface of the gelatin. Suitable drying was achieved, for example, at room temperature or on a hotplate at a moderate temperature (e.g., 80° C.). The substrates were then fixed to prevent the darkening of the silver nitrate in natural light. A typical fixer solution concentration is 20% (volumetric—60 ml of ILFORD's Rapid Fixer solution in 240 ml of DI water). The fixing process included contacting the substrates with fixer solution for 60-90 s, dipping the substrates into a water bath for 30-45 s, and then drying the substrates on a hot plate at 80° C.

In some implementations, a substrate with gel-grown dendrites can be cut to yield individual tags. The tags can be affixed to an item (e.g., packaging) to identify the item. FIG. 14A depicts a container 1400 including dendritic structure 1402 affixed to label 1404. The container 1400 can be configured to contain a liquid or a solid product. In some implementations, a water-permeable gel layer can be applied directly to an item (e.g., packaging, a container, a pharmaceutical product, or a food product), or an item can otherwise include a water-permeable gel layer (e.g., the item is formed of a water-permeable gel layer), and the water-permeable gel layer electrochemically activated (e.g., as described with respect to FIGS. 13A and 13B), such that dendritic structures can be grown in-situ on the item. FIG. 14B depicts vessel 1410 (e.g., a capsule) having a body 1412 and a cap 1414. The body 1412 is configured to hold a solid substance (e.g., a pharmaceutical product), and the cap 1414 has an inside diameter configured to fit around the outside diameter of the body 1412, and thereby contain a solid substance in the vessel 1410. The body 1412 and the cap 1414 are typically formed of gelatin. In some implementations, electrodes 1416 may be printed directly on the body 1412 or the cap 1414 to facilitate growth of a dendritic structure 1418 directly on a surface of the body or the cap of the vessel 1410 prior to filling. In one example, the dendritic structure 1418 is formed by a process such as that described with respect to FIG. 13A.

The dendritic structures and tags disclosed herein have complex structures, no two of which are precisely identical. Because each dendritic structure is unique, a tag containing the structure can be affixed to an article to act as a "fingerprint" that uniquely identifies the article. Moreover, because dendritic tags can be economically fabricated in large volumes and protected against degradation, duplication, and removal, they are particularly well suited for use in commercial transactions, where identification and authentication of goods is of great importance to many commercial entities.

OTHER EMBODIMENTS

A number of embodiments have been described. Nevertheless, it will be understood that various modifications may be made without departing from the spirit and scope of the disclosure. Accordingly, other embodiments are within the scope of the following claims.

What is claimed is:

1. A method of forming dendritic structures, the method comprising:
    printing an electrically conductive ink on a substrate to form a multiplicity of pairs of electrodes on the substrate;
    curing the multiplicity of pairs of electrodes;
    immersing the substrate into an electrolytic solution;
    applying an electrical potential to the multiplicity of pairs of electrodes to form a multiplicity of dendritic structures on the substrate;
    passing the substrate through a rinse bath to remove excess electrolyte;
    passing the substrate through a fixing bath to chemically deactivate residual electrolyte material in or on the substrate;
    drying the multiplicity of dendritic structures;
    oxidizing the multiplicity of dendritic structures;
    applying a coating material to the multiplicity of dendritic structures; and
    cutting the substrate to yield a multiplicity of substrate pieces, each substrate piece comprising one or more of the multiplicity of dendritic structures.

2. The method of claim 1, wherein the substrate comprises one or more materials selected from the group consisting of synthetic and non-synthetic paper and card materials, polyethylene, polypropylene, polyester, polystyrene, polyamide, polyolefin, acetate, cellulose acetate, acrylate, vinyl, polyester, and polyethylene terephthalate.

3. The method of claim 1, wherein the substrate comprises a first structural material and a second adsorbent material.

4. The method of claim 3, wherein the first structural material comprises at least one of a polymeric material, a paper material, and a cloth material.

5. The method of claim 3, wherein the second adsorbent material comprises silica.

6. The method of claim 3, wherein the second adsorbent material is positioned at least partially within a body of the first structural material.

7. The method of claim 3, wherein the second adsorbent material comprises a gel.

8. The method of claim 1, wherein the electrical potential is applied to the multiplicity of pairs of electrodes for a period of between 1 second and 30 seconds.

9. The method of claim 1, wherein each dendritic structure of the multiplicity of dendritic structures is formed between a pair of multiplicity of pairs of electrodes, and a potential difference between the electrodes in each pair of electrodes is between 2 volts and 20 volts.

10. The method of claim 1, wherein the fixing bath comprises a thiosulfate-based fixing solution.

11. The method of claim 10, wherein the fixing solution comprises sodium thiosulfate or ammonium thiosulfate.

12. The method of claim 1, wherein oxidizing the dendritic structures comprises heating the multiplicity of dendritic structures to a temperature of between 90 degrees C. and 100 degrees C.

13. The method of claim 1, wherein the coating material comprises at least one material selected from the group consisting of cyanoacrylate, polymethylmethacrylate, polyethylene terephthalate, polysiloxane, silicon dioxide, silicon nitride, polyvinylchloride, and cellulose acetate.

* * * * *